(12) United States Patent
Misawa et al.

(10) Patent No.: US 11,666,920 B2
(45) Date of Patent: Jun. 6, 2023

(54) METHOD OF CLEANING ASPIRATION TUBE AND SPECIMEN MEASURING APPARATUS

(71) Applicant: SYSMEX CORPORATION, Kobe (JP)

(72) Inventors: Kota Misawa, Kobe (JP); Masaki Shiba, Kobe (JP); Hiroki Kotake, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 374 days.

(21) Appl. No.: 16/831,869

(22) Filed: Mar. 27, 2020

(65) Prior Publication Data
US 2020/0306804 A1    Oct. 1, 2020

(30) Foreign Application Priority Data
Mar. 28, 2019  (JP) .............................. JP2019-062502

(51) Int. Cl.
| | | |
|---|---|---|
| *B08B 9/023* | (2006.01) | |
| *B08B 3/04* | (2006.01) | |
| *G01N 35/10* | (2006.01) | |
| *A61M 1/00* | (2006.01) | |

(52) U.S. Cl.
CPC ............... *B01L 13/02* (2019.08); *B08B 3/04* (2013.01); *B08B 9/023* (2013.01); *G01N 35/1004* (2013.01); *A61M 1/84* (2021.05)

(58) Field of Classification Search
CPC ........... B08B 9/023; B08B 3/04; B08B 3/022; B08B 3/041; A61M 1/84; B01L 13/02; B01L 2200/0615; G01N 35/1004
See application file for complete search history.

(56) References Cited

U.S. PATENT DOCUMENTS

| | | | |
|---|---|---|---|
| 2003/0223472 A1* | 12/2003 | Ravalico | G01N 35/1016 374/31 |
| 2011/0171069 A1* | 7/2011 | Mishima | G01N 35/1004 422/62 |
| 2015/0192601 A1 | 7/2015 | Cohen | |

FOREIGN PATENT DOCUMENTS

| | | | | |
|---|---|---|---|---|
| EP | 2390669 A2 * | 11/2011 | ......... | G01N 35/1004 |
| JP | H07-333230 A | 12/1995 | | |
| JP | H09-274048 A | 10/1997 | | |
| JP | 2005081208 A * | 3/2005 | ............. | B01L 99/00 |
| JP | 2008-281480 A | 11/2008 | | |
| JP | 2012-008123 A | 1/2012 | | |

(Continued)

OTHER PUBLICATIONS

The Japanese Office Action (JPOA) dated Mar. 3, 2020 in a counterpart Japanese patent application.

(Continued)

*Primary Examiner* — Alexander Markoff
(74) *Attorney, Agent, or Firm* — Metrolex IP Law Group, PLLC

(57) ABSTRACT

A method of cleaning an aspiration tube in a specimen measuring apparatus includes: moving the aspiration tube while discharging a cleaning liquid onto an outer side surface of the aspiration tube; stopping the aspiration tube in a state where a tip of the aspiration tube or a droplet attached to the tip contacts a surface of a flow of the cleaning liquid; and moving the stopped aspiration tube in a direction away from the surface of the flow of the cleaning liquid.

10 Claims, 19 Drawing Sheets

(56) References Cited

FOREIGN PATENT DOCUMENTS

| JP | 2012-047504 A | | 3/2012 | |
|---|---|---|---|---|
| JP | 2014167401 A | * | 9/2014 | ......... G01N 35/1004 |
| JP | 2014-190809 A | | 10/2014 | |
| JP | 2015-017935 A | | 1/2015 | |
| JP | 2019105510 A | * | 6/2019 | ............. G01N 33/49 |
| JP | 6542557 B2 | * | 7/2019 | ............... G01N 1/38 |
| WO | 2008/108328 A1 | | 9/2008 | |
| WO | 2010/016506 A1 | | 2/2010 | |
| WO | 2016/170994 A1 | | 10/2016 | |

OTHER PUBLICATIONS

An Office Action dated Jun. 23, 2020 in a counterpart Japanese patent application.

* cited by examiner

FIG. 16

| | BETWEEN CLEANING LIQUID CHAMBER AND PRESSURE SYRINGE | BETWEEN PRESSURE SYRINGE AND BRANCHING PART | DISCHARGE OF CLEANING LIQUID INTO ASPIRATION TUBE | DISCHARGE OF CLEANING LIQUID BY CLEANING LIQUID DISCHARGER | DRAINAGE OF CLEANING LIQUID FROM FIRST VESSEL | METERING SYRINGE | PRESSURE SYRINGE | VERTICAL MOVEMENT OF ASPIRATION TUBE (DRIVEN BY MOTOR) | REMARKS |
|---|---|---|---|---|---|---|---|---|---|
| | 198a | 198b | 199a/199b | 193 | 194 | 15a/15b | 196 | 45a/45b | REFERENCE SIGN |
| t0 | | | | | | | | | |
| t1 | CLOSE | | | | | | | | |
| t2 | | OPEN | OPEN | OPEN | OPEN | | | LOWER | MOVE DOWNWARD TO CLEANING POSITION H2 |
| t3 | | | | | | | | | |
| t4 | | | | | | DISCHARGE | DISCHARGE | | |
| t5 | OPEN | | | | | | | | |
| t6 | | | | | | | | RAISE | CLEAN ENTIRE CLEANING TARGET AREA WITH UPWARD AND DOWNWARD MOVEMENTS |
| t7 | | | | | | | | LOWER | |
| t8 | | | | | | | | | |
| t9 | | | | | | | | RAISE | MOVE UPWARD TO POSITION H1 AT WHICH CONTACT IS MADE WITH SURFACE OF CLEANING LIQUID |
| t10 | | | | | | | | | STOP ASPIRATION TUBE |
| t11 | | | | | | | | | |
| t12 | | CLOSE | CLOSE | CLOSE | CLOSE | | | RAISE | MOVE UPWARD TO HOME POSITION H0 |
| t13 | | | | | | | | | |
| t14 | | | | | | | | | |
| t15 | | | | | | | | | |

METHOD OF CLEANING ASPIRATION TUBE AND SPECIMEN MEASURING APPARATUS

CROSS REFERENCE TO RELATED APPLICATIONS

This application claims priority from to prior Japanese Patent Application No. 2019-062502 filed with the Japan Patent Office on Mar. 28, 2019, the entire contents of which are incorporated herein by reference.

BACKGROUND

The disclosure relates to a method of cleaning an aspiration tube in a specimen measuring apparatus.

Techniques of cleaning an aspiration tube used in a specimen measuring apparatus have heretofore been known (see Japanese Patent Application Publication No. 2008-281480 ("Patent Literature 1"), for example).

Patent Literature 1 discloses a nozzle cleaning apparatus which, as illustrated in FIG. 24, has: a cleaning vessel 903 having in its top an opening 902 into which to insert a dispensing nozzle 901 that dispenses a sample or a reagent; cleaning liquid supply units 904 that discharge a cleaning liquid from an upper portion of the inside of the cleaning vessel 903; and a reservoir part 905 located under the cleaning vessel 903, having in its top an opening into which to insert the dispensing nozzle 901, and having the cleaning liquid accumulated therein. In Patent Literature 1, the cleaning liquid is discharged from the cleaning liquid supply units 904 to clean the outer wall surface of the dispensing nozzle 901 moved downward from the opening 902. Further, the dispensing nozzle 901 is immersed in the cleaning liquid accumulated in the reservoir part 905. Thereafter, the dispensing nozzle 901 is pulled up from the reservoir part 905 while the cleaning liquid is supplied from the cleaning liquid supply units 904.

Here, in the case where the dispensing nozzle 901 is pulled up while the outer wall surface of the dispensing nozzle 901 is cleaned as in Patent Literature 1, a droplet of the cleaning liquid may remain at the tip of the dispensing nozzle 901 when the tip of the dispensing nozzle 901 is pulled out of the cleaning liquid. If the next dispensing operation is performed with the droplet of the cleaning liquid remaining at the tip, the droplet contacts the sample or reagent to be newly aspirated. Thus, the cleaning liquid contained in the droplet may dilute the sample or reagent to be newly aspirated. The dilution may affect the measurement result particularly when the amount of the sample or the like to be dispensed is small. Moreover, if a residual sample or a residual reagent that remains after the cleaning is present in the droplet remaining at the tip of the dispensing nozzle 901, the residual sample or the residual reagent in the droplet may be mixed into the sample or reagent to be newly aspirated.

Thus, it is desired to prevent a droplet from remaining at the tip of an aspiration tube that dispenses a sample or a reagent after cleaning of the aspiration tube.

One or more aspects aim to prevent a droplet from remaining at the tip of an aspiration tube that dispenses a sample or a reagent after cleaning of the aspiration tube.

SUMMARY

A method of cleaning an aspiration tube in a specimen measuring apparatus, according to one or more aspects, may include: (i) moving the aspiration tube while discharging a cleaning liquid onto an outer side surface of the aspiration tube, and stopping the aspiration tube in a state where a tip of the aspiration tube or a droplet attached to the tip contacts a surface of a flow of the cleaning liquid; and (ii) moving the stopped aspiration tube in a direction away from the surface of the flow of the cleaning liquid.

A method of cleaning an aspiration tube in a specimen measuring apparatus, according to one or more aspects, may include: obtaining position information on a position of the aspiration tube at which a tip of the aspiration tube or a droplet attached to the tip contacts a surface of a flow of a cleaning liquid, before discharge of the cleaning liquid onto an outer side surface of the aspiration tube; moving the aspiration tube while discharging the cleaning liquid onto the outer side surface of the aspiration tube, and decelerating or stopping the aspiration tube based on the position information; and moving the decelerated or stopped aspiration tube in a direction away from the surface of the flow of the cleaning liquid.

A specimen measuring apparatus according to one or more aspects may include: a measurement unit that measures a specimen prepared from a sample and a reagent; an aspiration tube that aspirates at least one of the sample or the reagent; a movement mechanism that moves the aspiration tube; a cleaning mechanism comprising a cleaning liquid discharger that discharges a cleaning liquid for cleaning the aspiration tube; and a controller that causes the movement mechanism to move the aspiration tube while causing the cleaning liquid discharger to discharge the cleaning liquid onto an outer side surface of the aspiration tube, to stop the aspiration tube in a state where a tip of the aspiration tube or a droplet attached to the tip contacts a surface of a flow of the cleaning liquid, and to move the stopped aspiration tube in a direction away from the surface of the flow of the cleaning liquid.

A specimen measuring apparatus according to one or more aspects may include: a measurement unit that measures a specimen prepared from a sample and a reagent; an aspiration tube that aspirates at least one of the sample or the reagent; a movement mechanism that moves the aspiration tube; a cleaning mechanism comprising a cleaning liquid discharger that discharges a cleaning liquid for cleaning the aspiration tube; a liquid surface detector that detects contact of a tip of the aspiration tube or a droplet attached to the tip with a surface of a flow of the cleaning liquid; and a controller. The controller obtains position information on a position of the aspiration tube at which the tip of the aspiration tube or the droplet attached to the tip contacts the surface of the flow of the cleaning liquid, based on a result of the detection by the liquid surface detector before discharge of the cleaning liquid onto an outer side surface of the aspiration tube from the cleaning liquid discharger, and causes the movement mechanism to move the aspiration tube while causing the cleaning liquid discharger to discharge the cleaning liquid onto the outer side surface of the aspiration tube, to decelerate or stop the aspiration tube based on the position information, and to move the decelerated or stopped aspiration tube in a direction away from the surface of the flow of the cleaning liquid.

BRIEF DESCRIPTION OF DRAWINGS

FIG. 16 is a diagram of a timing chart illustrating an operation illustrated in FIG. 15;

DETAILED DESCRIPTION

Figure 1A:
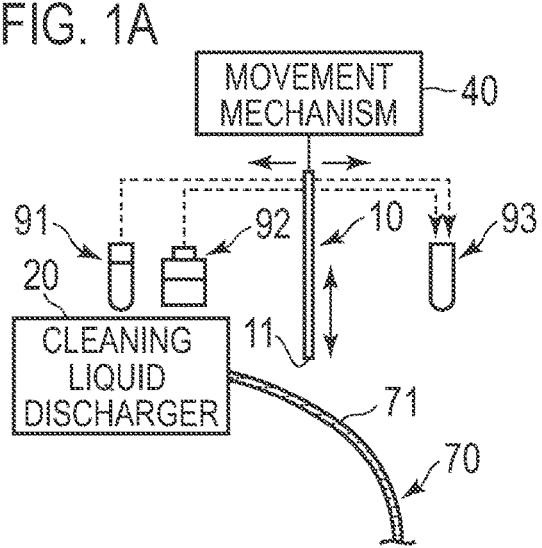
FIGS. 1A to 1F are schematic diagrams illustrating a sequence of operations in a method of cleaning an aspiration tube and a modification.

A method of cleaning an aspiration tube according to a first aspect is a method of cleaning an aspiration tube (10) in a specimen measuring apparatus (100), including, as illustrated in FIGS. 1 A to 1 F: moving the aspiration tube (10) while discharging a cleaning liquid (70) onto an outer side surface of the aspiration tube (10), and stopping the aspiration tube (10) in a state where a tip (11) of the aspiration tube (10) or a droplet (DL) attached to the tip (11) contacts a surface (71) of a flow of the cleaning liquid (70); and moving the stopped aspiration tube (10) in a direction away from the surface (71) of the flow of the cleaning liquid (70).

In the method of cleaning an aspiration tube (10) according to a first aspect, the above configuration enables the aspiration tube (10) to be stopped in the state where the tip (11) of the aspiration tube (10) or the droplet (DL) attached to the tip (11) contacts the surface (71) of the flow of the cleaning liquid (70). Thus, while the aspiration tube (10) is stopped, the cleaning liquid (70) attached to the outer side surface of the aspiration tube (10) converges to the tip (11) along the outer side surface of the aspiration tube (10) to thereby form the droplet (DL) at the tip 11, and the droplet (DL) is moved from the tip (11) side to the cleaning liquid (70) side by the surface tension of the cleaning liquid (70). This prevents the droplet (DL) from remaining at the tip (11) of the aspiration tube (10), which is to dispense a sample or a reagent, after the cleaning of the aspiration tube (10).

It may be preferable that the method of cleaning an aspiration tube (10) according to a first aspect include that, as illustrated in FIGS. 1 A to 1 F, the aspiration tube (10) is moved vertically, and the aspiration tube (10) is moved upward while the cleaning liquid (70) is discharged onto the outer side surface of the aspiration tube (10), and the aspiration tube (10) is stopped in the state where the tip (11) of the aspiration tube (10) or the droplet (DL) attached to the tip (11) contacts the surface (71) of the flow of the cleaning liquid (70). This configuration enables removal of the droplet (DL) attached to the tip (11) of the aspiration tube (10) with a minimum operation involving only moving the aspiration tube (10) upward at the end of the operation of cleaning the outer side surface of the aspiration tube (10).

Figure 12:
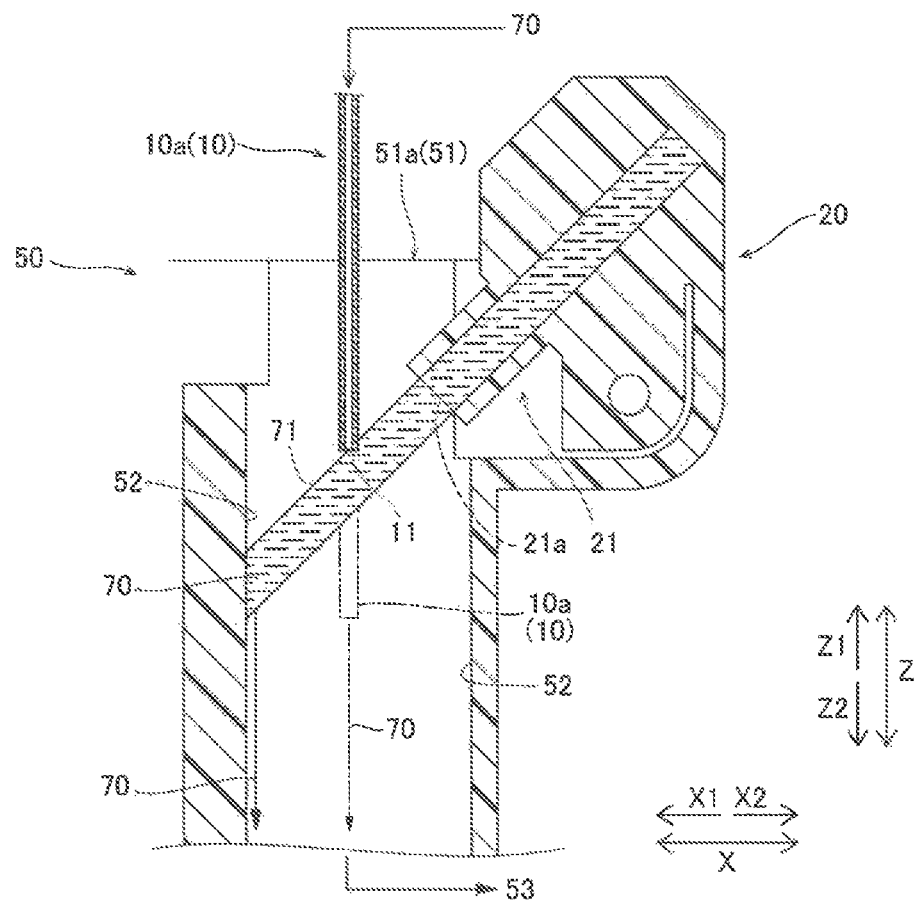
FIG. 12 is a diagram of an enlarged cross-sectional view illustrating cleaning inside a first vessel in a cleaning mechanism.

It may be preferable that the method of cleaning an aspiration tube (10) according to a first aspect include that, as illustrated in FIG. 12, the discharge of the cleaning liquid (70) onto the outer side surface of the aspiration tube (10) is performed inside a cleaning vessel (51), and the method further includes moving the aspiration tube (10) downward inside the cleaning vessel (51) while continuing the discharge of the cleaning liquid (70) onto the outer side surface of the aspiration tube (10) and drainage of the cleaning liquid (70) from the cleaning vessel (51). With this configuration, the aspiration tube (10) is not immersed in the cleaning liquid (70) accumulated in the cleaning vessel (51). The aspiration tube (10) is cleaned without contacting the cleaning liquid (70) accumulated in the cleaning vessel (51). This enables the aspiration tube (10) to avoid contacting the cleaning liquid (70) that has once contacted the aspiration tube (10) and taken dirt in and therefore effectively prevents the occurrence of contamination.

Figure 15:
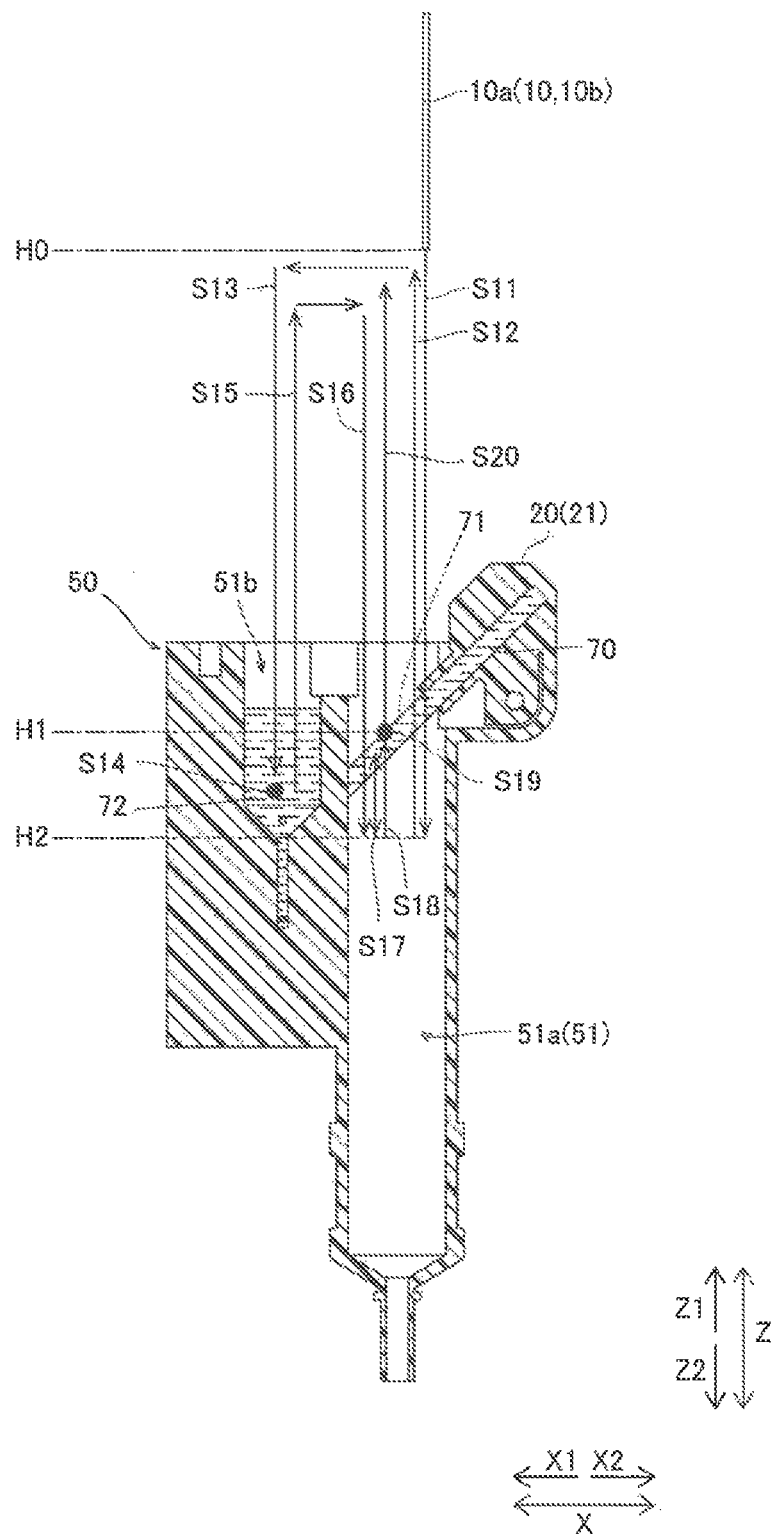
FIG. 15 is a diagram illustrating an example of operation of a specimen measuring apparatus by a method of cleaning an aspiration tube.

In this case, it may be preferable that, as illustrated in FIG. 15, the upward movement of the aspiration tube (10) be performed after the downward movement of the aspiration tube (10). With this configuration, the aspiration tube (10) is moved upward after the aspiration tube (10) is cleaned inside the cleaning vessel (51). This prevents the droplet (DL) from remaining at the tip (11) of the aspiration tube (10) even after the sufficient cleaning is performed.

It may be preferable that the method of cleaning an aspiration tube (10) according to a first aspect further include raising and lowering the aspiration tube (10) while maintaining, keeping or causing the aspiration tube (10) in contact with the flow of the cleaning liquid (70). With this configuration, since the aspiration tube (10) is raised and lowered, the portion of the aspiration tube (10) to be cleaned is brought into direct contact with the flow of the cleaning liquid (70) multiple times. This enables effective cleaning as compared to a case where the aspiration tube (10) is simply moved downward.

It may be preferable that the configuration including the moving of the aspiration tube (10) downward inside the cleaning vessel (51) include that, as illustrated in FIG. 16, in the moving of the aspiration tube (10) downward inside the cleaning vessel (51), the cleaning liquid (70) is discharged from the tip (11) into the cleaning vessel (51) by supplying the cleaning liquid (70) into the aspiration tube (10). With this configuration, the inner surface of the aspiration tube (10) is cleaned by the discharge of the cleaning liquid (70) from the tip (11) in parallel with the cleaning of the outer surface of the aspiration tube (10) with the cleaning liquid (70). Here, if the cleaning liquid (70) is accumulated in the cleaning vessel (51), the cleaning liquid (70) discharged from the tip (11) hits the liquid surface and the cleaning liquid (70) may be splashed and attached to the aspiration tube (10). However, even when the cleaning liquid (70) is discharged from the tip (11) into the cleaning vessel (51), the continuous drainage of the cleaning liquid (70) from the cleaning vessel (51) prevents the re-attachment of the cleaning liquid (70) to the aspiration tube (10).

Figure 17:
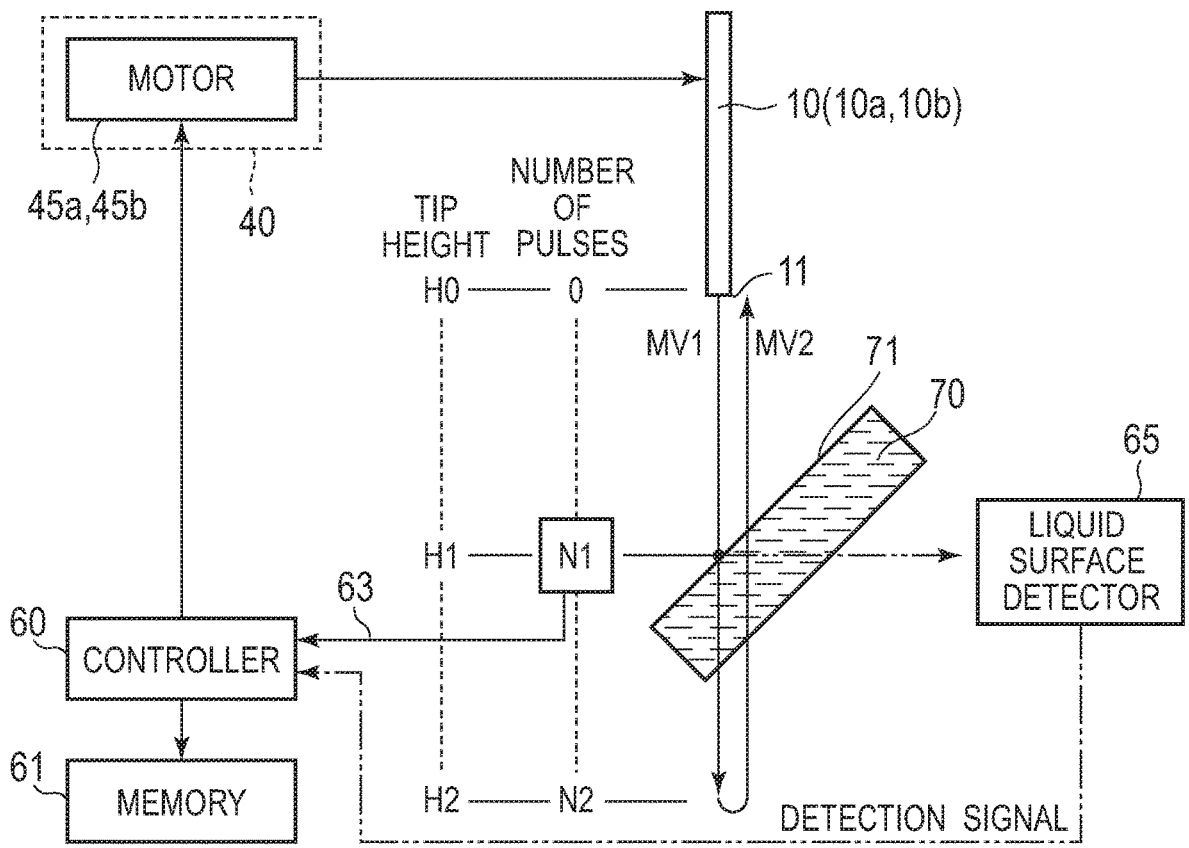
FIG. 17 is a schematic diagram illustrating an operation of obtaining position information on a position at which a tip contacts a surface of a cleaning liquid.
Figure 19:
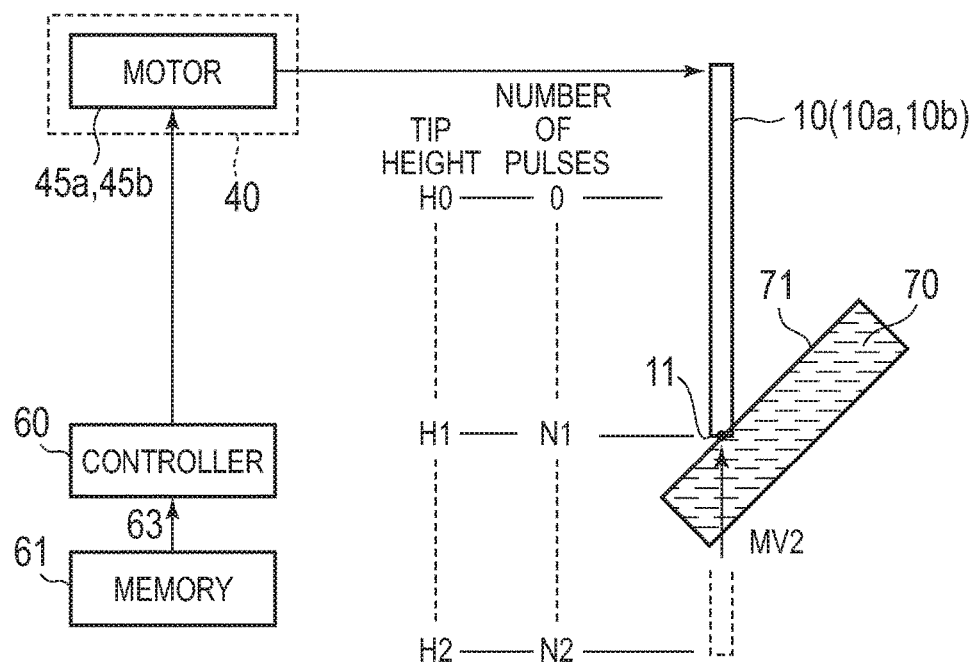
FIG. 19 is a schematic diagram illustrating an operation in cleaning of an aspiration tube.

It may be preferable that the method of cleaning an aspiration tube (10) according to a first aspect, as illustrated in FIGS. 17 and 19, further include obtaining position information (63) on a position of the aspiration tube (10) at which the tip (11) of the aspiration tube (10) or a droplet (DL) attached to the tip (11) contacts the surface (71) of the flow of the cleaning liquid (70), before the discharge of the cleaning liquid (70) onto the outer side surface of the aspiration tube (10), and the aspiration tube (10) be stopped based on the position information (63) in the state where the tip (11) of the aspiration tube (10) or the droplet (DL) attached to the tip (11) contacts the surface (71) of the flow of the cleaning liquid (70). With this configuration, unlike a case where, for example, the liquid surface is detected during the cleaning of the aspiration tube (10) to detect the position at which the tip (11) or the droplet (DL) attached to the tip (11) contacts the surface (71) of the flow of the cleaning liquid (70), the tip (11) or the droplet (DL) attached to the tip (11) is brought into contact with the surface (71) of the flow of the cleaning liquid (70) only by moving and stopping the aspiration tube (10) to and at a position obtained in advance. This eliminates the need to, for example, move the aspiration tube (10) at low speed for detection of the liquid surface, and thus enables the tip (11) or the droplet (DL) attached to the tip (11) to be brought into contact with the surface (71) of the flow of the cleaning liquid (70) in as short a time as possible. Accordingly, a longer time can be allotted for the cleaning of the aspiration tube (10).

In this case, it may be preferable that, as illustrated in FIG. 17, in the obtaining of the position information (63), contact of the tip (11) of the aspiration tube (10) or the droplet (DL) attached to the tip (11) with the surface (71) of the flow of the cleaning liquid (70) be detected with a liquid surface detector (65), and the position information (63) be obtained based on a result of the detection by the liquid surface detector (65). With this configuration, obtained is the position at which the tip (11) or the droplet (DL) attached to the tip (11) actually contacted the surface (71) of the flow of the cleaning liquid (70), and therefore the position information (63) is accurately obtained.

It may be preferable that the configuration involving detecting contact of the tip (11) with the surface (71) of the flow of the cleaning liquid (70) with the liquid surface detector (65) include that, as illustrated in FIGS. 17 and 19, in the obtaining of the position information (63), the aspiration tube (10) is moved downward from above the flow of the discharged cleaning liquid (70) to thereby bring the tip (11) or the droplet (DL) attached to the tip (11) into contact with the cleaning liquid (70), and in the cleaning of the aspiration tube (10), the aspiration tube (10) is moved upward based on the position information (63) from a position at which the flow of the cleaning liquid (70) contacts a portion above the tip (11) to the position at which the tip (11) or the droplet (DL) attached to the tip (11) contacts the surface (71) of the flow of the cleaning liquid (70). With this configuration, in the cleaning of the aspiration tube (10), the tip (11) or the droplet (DL) attached to the tip (11) is brought into contact with the surface (71) of the flow of the cleaning liquid (70) more reliably based on the obtained position information (63). Specifically, in the detection of contact between the tip (11) or the droplet (DL) attached to the tip (11) and the liquid surface, detected is the change in a detection signal either at a moment when the aspiration tube (10) or the droplet (DL) and the cleaning liquid (70) transition from a non-contacting state to a contacting state or at a moment when the aspiration tube (10) or the droplet (DL) and the cleaning liquid (70) transition from the contacting state to the non-contacting state as a result of moving the aspiration tube (10). Here, since the cleaning liquid (70) is not stationary but is forming a flow, the detection signal is not stable while the cleaning liquid (70) and the aspiration tube (10) or the droplet (DL) are in the contacting state. This makes it difficult to accurately detect transition to the non-contacting state. However, the contact position can be accurately detected by bringing the aspiration tube (10) into contact with the cleaning liquid (70) by moving the aspiration tube (10) downward from above in the non-contacting state. Also, a mechanism that moves the aspiration tube (10) entails error factors such as the backlash of gears used to transmit a motor's power, for example. For this reason, in the case of moving the aspiration tube (10) via upward movement from below in its cleaning toward the position detected in the obtaining of the position information (63) via downward movement from above, the backlash may cause displacement to a slightly lower position than the detected position. In this case, the displacement occurs in a direction toward the flow of the cleaning liquid (70). Hence, even with the error factor taken into consideration, the tip (11) or the droplet (DL) attached to the tip (11) is reliably brought into contact with the surface (71) of the flow of the cleaning liquid (70).

It may be preferable that the method of cleaning an aspiration tube (10) according to a first aspect include that, as illustrated in FIG. 12, when the cleaning liquid (70) is discharged onto the outer side surface of the aspiration tube (10), the cleaning liquid (70) is discharged obliquely downward to thereby form a substantially straight columnar flow of the cleaning liquid (70). With this configuration, the cleaning liquid (70) is discharged obliquely downward. Therefore, the variation in the position of the surface of the cleaning liquid (70) due to subtle changes in hydraulic pressure or the like is reduced as compared to a case where the cleaning liquid (70) is discharged upward, for example. Moreover, since the discharge pressure obtained is so high that the flow of the cleaning liquid (70) forms a substantially straight columnar shape, the subtle changes in hydraulic pressure or the like have a low impact. This also reduces the variation in the position of the surface of the cleaning liquid (70).

It may be preferable that the method of cleaning an aspiration tube (10) according to a first aspect, as illustrated in FIG. 15, further include cleaning the aspiration tube (10) with a second cleaning liquid (72) higher in detergency than the cleaning liquid (70), and the cleaning of the aspiration tube (10) with the cleaning liquid (70) be performed after the cleaning of the aspiration tube (10) with the second cleaning liquid (72). With this configuration, the cleaning with the cleaning liquid (70) and the removal of the droplet (DL) are performed after the cleaning with the second cleaning liquid (72) with higher detergency. Hence, in the case of performing the cleaning with the second cleaning liquid (72) with higher detergency, not only contamination by the droplet (DL) is prevented but also contamination by the cleaning component contained in the second cleaning liquid (72) is prevented.

Figure 2:
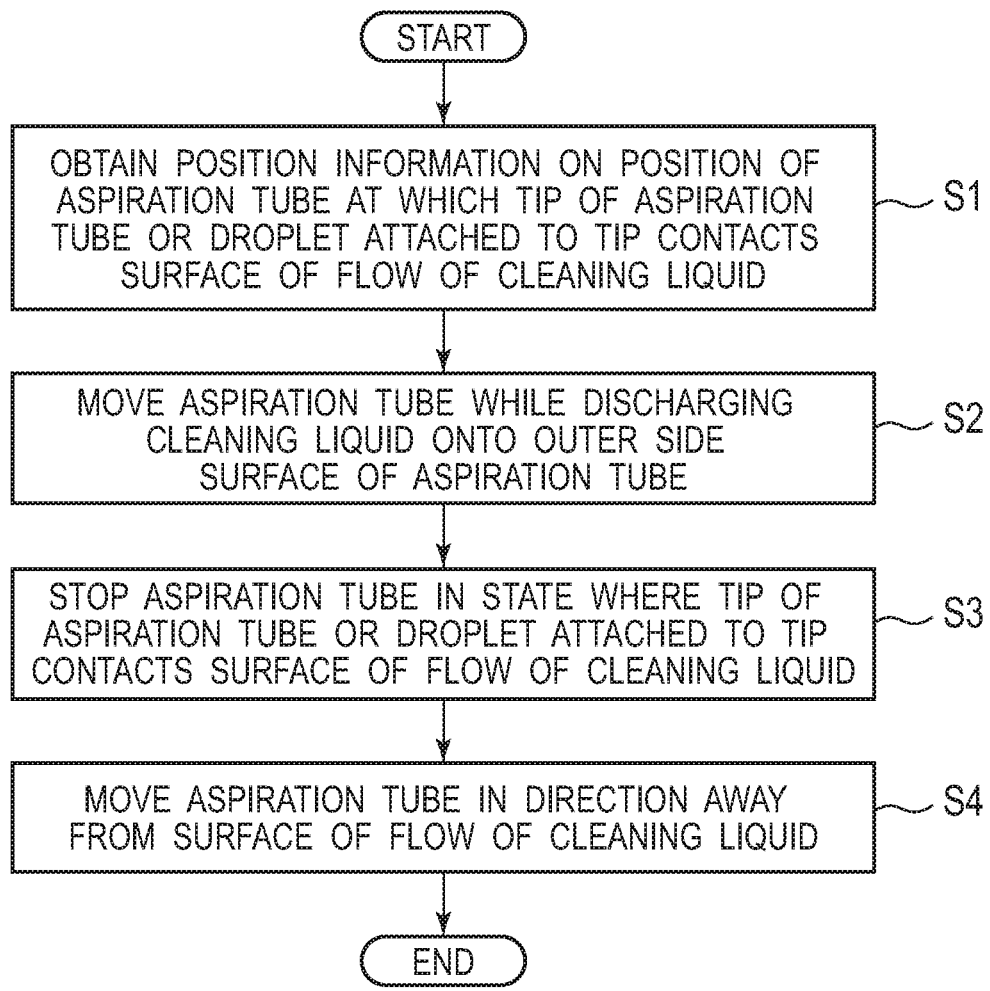
FIG. 2 is a flow diagram illustrating a method of cleaning an aspiration tube.

A method of cleaning an aspiration tube according to a second aspect is a method of cleaning an aspiration tube (10) in a specimen measuring apparatus (100), including, as illustrated in FIG. 2: obtaining position information (63) on a position of the aspiration tube (10) at which a tip (11) of the aspiration tube (10) or a droplet (DL) attached to the tip (11) contacts a surface (71) of a flow of a cleaning liquid (70), before discharge of the cleaning liquid (70) onto an outer side surface of the aspiration tube (10); moving the aspiration tube (10) while discharging the cleaning liquid (70) onto the outer side surface of the aspiration tube (10), and decelerating or stopping the aspiration tube (10) based on the position information (63); and moving the decelerated or stopped aspiration tube (10) in a direction away from the surface (71) of the flow of the cleaning liquid (70).

In the method of cleaning an aspiration tube according to a second aspect, with the above configuration, based on the position information (63), the aspiration tube (10) is accurately moved to the position at which the tip (11) of the aspiration tube (10) or the droplet (DL) attached to the tip 11 contacts the surface (71) of the flow of the cleaning liquid (70). Then, while the aspiration tube (10) is decelerated or stopped based on the position information (63), the cleaning liquid (70) attached to the outer side surface of the aspiration tube (10) converges to the tip (11) along the outer side surface of the aspiration tube (10) to thereby form the droplet (DL) at the tip (11), and the droplet (DL) is moved from the tip (11) side to the cleaning liquid (70) side by the surface tension of the cleaning liquid (70). This prevents the droplet (DL) from remaining at the tip (11) of the aspiration tube (10), which is to dispense a sample or the reagent, after the cleaning of the aspiration tube (10).

Figure 3:
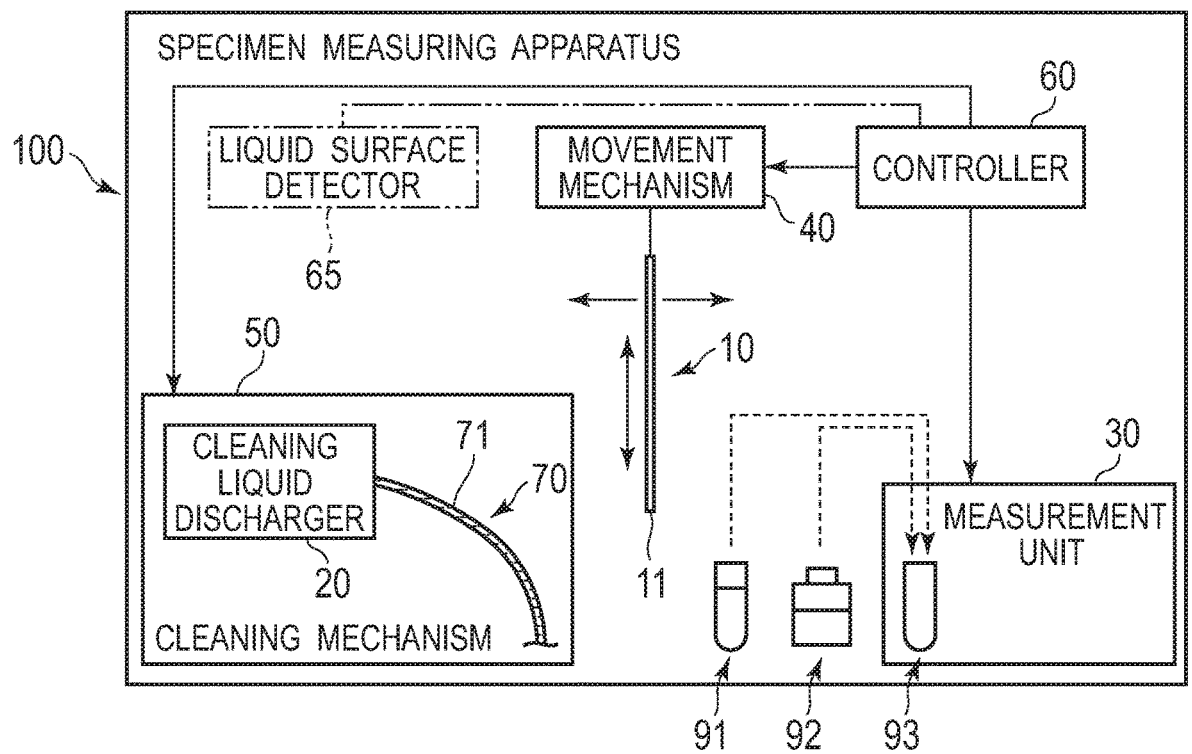
FIG. 3 is a schematic diagram illustrating an overview of a specimen measuring apparatus.

A specimen measuring apparatus (100) according to a third aspect includes, as illustrated in FIG. 3: a measurement unit (30) that measures a specimen prepared to contain a sample and a reagent; an aspiration tube (10) that aspirates at least one of the sample or the reagent; a movement mechanism (40) that moves the aspiration tube (10); a cleaning mechanism (50) including a cleaning liquid discharger (20) that discharges a cleaning liquid (70) for cleaning the aspiration tube (10); and a controller (60) that, in cleaning of the aspiration tube (10), controls the movement mechanism (40) so as to move the aspiration tube (10) while causing the cleaning liquid discharger (20) to discharge the cleaning liquid (70) onto an outer side surface of the aspiration tube (10), stop the aspiration tube (10) in a state where a tip (11) of the aspiration tube (10) or a droplet (DL) attached to the tip (11) contacts a surface (71) of a flow of the cleaning liquid (70), and move the stopped aspiration tube (10) in a direction away from the surface (71) of the flow of the cleaning liquid (70).

By being configured as above, the specimen measuring apparatus (100) according to a third aspect brings about advantageous effects similar to those by a first aspect.

It may be preferable that the specimen measuring apparatus (100) according to a third aspect be such that, as illustrated in FIGS. 1 A to 1 F, the movement mechanism (40) vertically moves the aspiration tube (10), and the controller (60) controls the movement mechanism (40) so as to move the aspiration tube (10) upward while causing the cleaning liquid discharger (20) to discharge the cleaning liquid (70) onto the outer side surface of the aspiration tube (10), and stop the aspiration tube (10) in the state where the tip (11) of the aspiration tube (10) or the droplet (DL) attached to the tip (11) contacts the surface (71) of the flow of the cleaning liquid (70). This configuration enables removal of the droplet (DL) attached to the tip (11) of the aspiration tube (10) with a minimum operation involving only moving the aspiration tube (10) upward at the end of the operation of cleaning the outer side surface of the aspiration tube (10).

In this case, it may be preferable that, as illustrated in FIG. 12, the cleaning mechanism (50) further include a cleaning vessel (51) opened at a top so as to receive the cleaning liquid (70) discharged from the cleaning liquid discharger (20), and the controller (60) cause the cleaning liquid discharger (20) to discharge the cleaning liquid (70) onto the outer side surface of the aspiration tube (10) inside the cleaning vessel (51), and control the movement mechanism (40) so as to move the aspiration tube (10) downward inside the cleaning vessel (51) while continuing the discharge of the cleaning liquid (70) onto the outer side surface of the aspiration tube (10) and drainage of the cleaning liquid (70) from the cleaning vessel (51). With this configuration, the aspiration tube (10) is not immersed in the cleaning liquid (70) accumulated in the cleaning vessel (51). The aspiration tube (10) is cleaned without contacting the cleaning liquid (70) accumulated in the cleaning vessel (51). This enables the aspiration tube (10) to avoid contacting the cleaning liquid (70) that has once contacted the aspiration tube (10) and taken dirt in and therefore effectively prevents the occurrence of contamination.

It may be preferable that the configuration in which the cleaning mechanism (50) includes the cleaning vessel (51) be such that, as illustrated in FIG. 15, the controller (60) controls the movement mechanism (40) so as to perform the upward movement of the aspiration tube (10) after the downward movement of the aspiration tube (10). With this configuration, the aspiration tube (10) is moved upward after the aspiration tube (10) is cleaned inside the cleaning vessel (51). This prevents the droplet (DL) from remaining at the tip (11) of the aspiration tube (10) even after the sufficient cleaning is performed.

In this case, it may be preferable that, as illustrated in FIG. 16, the specimen measuring apparatus further include a cleaning liquid supply unit (195) that supplies the cleaning liquid (70) to the aspiration tube (10), and the controller (60) perform control that causes the cleaning liquid (70) to be discharged into the cleaning vessel (51) from the tip (11) by supplying the cleaning liquid (70) into the aspiration tube (10) when moving the aspiration tube (10) downward inside the cleaning vessel (51). With this configuration, the inner surface of the aspiration tube (10) is cleaned by the discharge of the cleaning liquid (70) from the tip (11) in parallel with the cleaning of the outer surface of the aspiration tube (10) with the cleaning liquid (70) discharged from the cleaning liquid discharger (20). Here, if the cleaning liquid (70) is accumulated in the cleaning vessel (51), the cleaning liquid (70) discharged from the tip (11) hits the liquid surface and the cleaning liquid (70) may be splashed and attached to the aspiration tube (10). However, even when the cleaning liquid (70) is discharged from the tip (11) into the cleaning vessel (51), the continuous drainage of the cleaning liquid (70) from the cleaning vessel (51) prevents the re-attachment of the cleaning liquid (70) to the aspiration tube (10).

It may be preferable that, as illustrated in FIGS. 17 and 19, the specimen measuring apparatus (100) according to a third aspect further include a liquid surface detector (65) that detects contact of the tip (11) of the aspiration tube (10) or a droplet (DL) attached to the tip (11) with the surface (71) of the flow of the cleaning liquid (70), and the controller (60) obtain position information (63) on a position of the aspiration tube (10) at which the tip (11) of the aspiration tube (10) or the droplet (DL) attached to the tip (11) contacts the surface (71) of the flow of the cleaning liquid (70), based on a result of the detection by the liquid surface detector (65) before the discharge of the cleaning liquid (70) onto the outer side surface of the aspiration tube (10) from the cleaning liquid discharger (20), and based on the position information (63), perform control that stops the aspiration tube (10) in the state where the tip (11) of the aspiration tube (10) or the droplet (DL) attached to the tip (11) contacts the surface (71) of the flow of the cleaning liquid (70). With this configuration, unlike a case where the position information (63) is obtained via non-contact detection such as image recognition or laser measurement, for example, obtained is the position at which the tip (11) or the droplet (DL) attached to the tip (11) actually contacted the surface (71) of the flow of the cleaning liquid (70), and therefore the position information (63) is accurately obtained. Then, in the cleaning of the aspiration tube (10), the tip (11) or the droplet (DL) attached to the tip (11) is brought into contact with the surface (71) of the flow of the cleaning liquid (70) only by moving and stopping the aspiration tube (10) to and at a position obtained in advance. This eliminates the need to, for example, move the aspiration tube (10) at low speed for detection of the liquid surface, and thus enables the tip (11) or the droplet (DL) attached to the tip (11) to be brought into contact with the surface (71) of the flow of the cleaning liquid (70) in as short a time as possible. Accordingly, a longer time can be allotted for the cleaning of the aspiration tube (10).

In this case, it may be preferable that, as illustrated in FIGS. 17 and 19, in the obtaining of the position information (63), the controller (60) control the movement mechanism (40) so as to move the aspiration tube (10) downward from above the flow of the discharged cleaning liquid (70) to thereby bring the tip (11) or the droplet (DL) attached to the tip (11) into contact with the cleaning liquid (70), and in the cleaning of the aspiration tube (10), the controller (60) control the movement mechanism (40) so as to move the aspiration tube (10) upward based on the position information (63) from a position (H2) at which the flow of the cleaning liquid (70) contacts a portion above the tip (11) to the position (H1) at which the tip (11) or the droplet (DL) attached to the tip (11) contacts the surface (71) of the flow of the cleaning liquid (70). With this configuration, in the cleaning of the aspiration tube (10), the tip (11) or the droplet (DL) attached to the tip (11) is brought into contact with the surface (71) of the flow of the cleaning liquid (70) more reliably based on the obtained position information (63). Specifically, in the detection of contact between the tip (11) or the droplet (DL) attached to the tip (11) and the liquid surface, detected is the change in a detection signal either at a moment when the aspiration tube (10) or the droplet (DL) and the cleaning liquid (70) transition from a non-contacting state to a contacting state or at a moment when the aspiration tube (10) or the droplet (DL) and the cleaning liquid (70) transition from the contacting state to the non-contacting state as a result of moving the aspiration tube (10). Here, since the cleaning liquid (70) is not stationary but is forming a flow, the detection signal is not stable while the cleaning liquid (70) and the aspiration tube (10) or the droplet (DL) are in the contacting state. This makes it difficult to accurately detect transition to the non-contacting state. However, the contact position can be accurately detected by bringing the aspiration tube (10) into contact with the cleaning liquid (70) by moving the aspiration tube (10) downward from above in the non-contacting state. Also, the movement mechanism (40) entails error factors such as the backlash of gears used to transmit a motor's power, for example. For this reason, in the case of moving the aspiration tube (10) via upward movement from below in its cleaning toward the position detected in the obtaining of the position information (63) via downward movement from above, the backlash may cause displacement to a slightly lower position than the detected position. In this case, the displacement occurs in a direction toward the flow of the cleaning liquid (70). Hence, even with the error factor taken into consideration, the tip (11) or the droplet (DL) attached to the tip (11) is reliably brought into contact with the surface (71) of the flow of the cleaning liquid (70).

It may be preferable that the specimen measuring apparatus (100) according to a third aspect be such that, as illustrated in FIG. 12, the cleaning liquid discharger (20) includes a discharge port facing obliquely downward, and forms a substantially straight columnar flow of the cleaning liquid (70). With this configuration, the cleaning liquid (70) is discharged obliquely downward. Therefore, the variation in the position of the surface of the cleaning liquid (70) due to subtle changes in hydraulic pressure or the like is reduced as compared to a case where the cleaning liquid (70) is discharged upward, for example. Moreover, since the discharge pressure obtained is so high that the flow of the cleaning liquid (70) forms a substantially straight columnar shape, the subtle changes in hydraulic pressure or the like have a low impact. This also reduces the variation in the position of the surface of the cleaning liquid (70).

It may be preferable that the specimen measuring apparatus (100) according to a third aspect be such that, as illustrated in FIG. 15, the cleaning liquid discharger (20) includes a first discharger (21) that discharges the cleaning liquid (70), and a second discharger (22) that discharges a second cleaning liquid (72) higher in detergency than the cleaning liquid (70), and the controller (60) controls the cleaning liquid discharger (20) so as to perform the cleaning of the aspiration tube (10) with the cleaning liquid (70) after cleaning of the aspiration tube (10) with the second cleaning liquid (72). With this configuration, the cleaning with the cleaning liquid (70) and the removal of the droplet (DL) are performed after the cleaning with the second cleaning liquid (72) with higher detergency. Hence, in the case of performing the cleaning with the second cleaning liquid (72) with higher detergency, not only contamination by the droplet (DL) is prevented but also contamination by the cleaning component contained in the second cleaning liquid (72) is prevented.

A specimen measuring apparatus (100) according to a fourth aspect includes, as illustrated in FIGS. 3 and 2: a measurement unit (30) that measures a specimen prepared from a sample and a reagent; an aspiration tube (10) that aspirates at least one of the sample or the reagent; a movement mechanism (40) that moves the aspiration tube (10); a cleaning mechanism (50) including a cleaning liquid discharger (20) that discharges a cleaning liquid (70) for cleaning the aspiration tube (10); a liquid surface detector (65) that detects contact of a tip (11) of the aspiration tube (10) or a droplet (DL) attached to the tip (11) with a surface (71) of a flow of the cleaning liquid (70); and a controller (60) that obtains position information (63) on a position of the aspiration tube (10) at which the tip (11) of the aspiration tube (10) or the droplet (DL) attached to the tip (11) contacts the surface (71) of the flow of the cleaning liquid (70), based on a result of the detection by the liquid surface detector (65) before discharge of the cleaning liquid (70) onto an outer side surface of the aspiration tube (10) from the cleaning liquid discharger (20), and controls the movement mechanism (40) so as to move the aspiration tube (10) while causing the cleaning liquid discharger (20) to discharge the cleaning liquid (70) onto the outer side surface of the aspiration tube (10), decelerate or stop the aspiration tube (10) based on the position information (63), and move the decelerated or stopped aspiration tube (10) in a direction away from the surface (71) of the flow of the cleaning liquid (70).

By being configured as above, the specimen measuring apparatus (100) according to a fourth aspect brings about advantageous effects similar to those by a second aspect.

It is possible to prevent a droplet from remaining at the tip of an aspiration tube that dispenses a sample or a reagent after cleaning of the aspiration tube.

Embodiments are described below with reference to the drawings.

[Overview of Method of Cleaning Aspiration Tube]

First, an overview of a method of cleaning an aspiration tube according to an embodiment is described with reference to FIGS. 1A to 1F.

The method of cleaning an aspiration tube according to an embodiment is a method of cleaning an aspiration tube 10 that performs aspiration and discharge of a liquid in a specimen measuring apparatus.

The specimen measuring apparatus is an apparatus that performs measurement on a sample collected from a patient, for example, for a laboratory examination or medical research.

The specimen measuring apparatus prepares measurement specimen by adding at least one predetermined type of reagent to a sample. The sample is a sample derived from a living body. The sample derived from a living body is, for example, a liquid collected from a subject, such as blood (whole blood, serum, or plasma), urine, or another body fluid, a liquid obtained by performing a predetermined pretreatment on a collected body fluid or blood, or the like. The sample may contain, for example, some tissues, cells, or the like of the subject that are not liquid. The sample undergoes measurement in a state of being stored in a sample container 91 into which an aspiration tube 10 can be inserted. The reagent is a liquid stored in a bottle-shaped reagent container 92 into which the aspiration tube 10 can be inserted.

The aspiration tube 10 is provided in the specimen measuring apparatus and dispenses a sample or the reagent to be used in the measurement. The dispensing refers to aspirating a liquid and discharging the liquid in a predetermined amount. The aspiration tube 10 is, for example, mounted to a movement mechanism 40 of the specimen measuring apparatus and is configured to be movable to a liquid aspirating position, a liquid discharging position, and a cleaning position. The aspiration tube 10 is a tubular member opened at both ends, and the opening at one end is open to the outside while the opening at the other end is connected to a fluid circuit. The aspiration tube 10 aspirates a liquid from the opening at the one end when negative pressure is supplied from the fluid circuit, and discharges the liquid from the opening at the one end when positive pressure is supplied from the fluid circuit. Note that the negative pressure is a pressure lower than the pressure of the outside while the positive pressure is a pressure higher than the pressure of the outside. The aspiration tube 10 aspirates a sample or the reagent from its container and discharges the aspirated liquid into a reaction container 93 that is different from the container of the sample or the reagent.

The aspiration tube 10 for dispensing a sample sequentially dispenses samples collected from different subjects. Depending on the measurement items, the aspiration tube 10 for dispensing a reagent dispenses different types of reagents. Each aspiration tube 10 is cleaned in order to prevent contamination in which the previously dispensed sample or reagent is mixed into the sample or reagent to be dispensed next. The method of cleaning the aspiration tube 10 is carried out after the dispensing of a liquid but before the dispensing of a different liquid. The cleaning does not necessarily have to be performed in the case of dispensing only the same sample multiple times or in the case of dispensing only the same type of reagent multiple times.

The method of cleaning the aspiration tube 10 in an embodiment includes steps S2 to S4 illustrated in FIG. 2. Specifically, the method of cleaning the aspiration tube 10 in an embodiment includes steps of: (S2) moving the aspiration tube 10 while discharging a cleaning liquid 70 onto the outer side surface of the aspiration tube 10; (S3) stopping the aspiration tube 10 in a state where a tip 11 of the aspiration tube 10 or a droplet DL attached to the tip 11 contacts a surface 71 of the flow of the cleaning liquid 70; and (S4) moving the stopped aspiration tube 10 in a direction away from the surface 71 of the flow of the cleaning liquid 70. As mentioned later, the method of cleaning the aspiration tube 10 in an embodiment may further include step 51 in FIG. 2.

In step S2, as illustrated in FIG. 1A, a cleaning liquid discharger 20 provided in the specimen measuring apparatus discharges the cleaning liquid 70 in a certain direction, for example.

The example of FIGS. 1A to 1F illustrates an instance in which the cleaning liquid discharger 20 discharges the cleaning liquid 70 in a lateral direction (horizontal direction). The cleaning liquid discharger 20 discharges the cleaning liquid 70 into the air. The cleaning liquid discharger 20 discharges the cleaning liquid 70 so as to form a flow of the cleaning liquid 70 flowing out along a certain trajectory. In the example of FIGS. 1A to 1F, the laterally discharged cleaning liquid 70 forms a parabolic flow falling with gravity. The flow of the cleaning liquid 70 is in the shape of a column or a line having the surface 71 as an interface between the flow and the air, and the inside of the surface 71 is filled with the cleaning liquid 70. The cleaning liquid discharger 20 continues discharging the cleaning liquid 70 at certain pressure, for example. The certain pressure here means keeping the pressure variation within a range within which the shape of the flow of the cleaning liquid 70 can be maintained to such an extent that the tip 11 of the aspiration tube 10 can be repeatedly or continuously in contact with the surface 71 of the flow of the cleaning liquid 70.

Figure 1B:
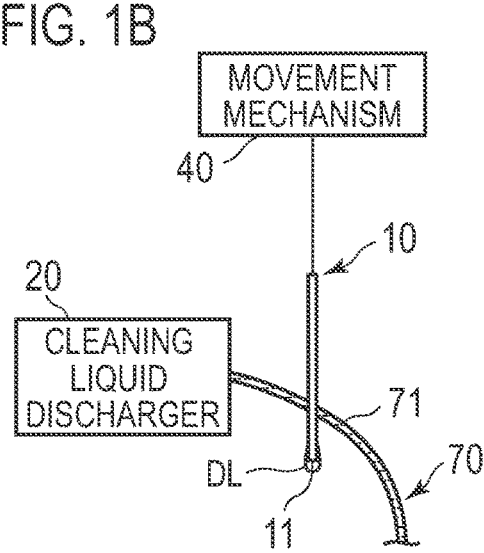

In step S2, the aspiration tube 10 contacts the cleaning liquid 70. As illustrated in FIG. 1B, the aspiration tube 10 is moved to a position at which the aspiration tube 10 directly contacts the flow of the cleaning liquid 70 by the movement mechanism 40, which is provided in the specimen measuring apparatus, for example. With a portion of the outer side surface of the aspiration tube 10 being positioned in the flow of the cleaning liquid 70, the portion in contact with the cleaning liquid 70 is cleaned. As a result, the aspiration tube 10 is cleaned by the flow of the cleaning liquid 70 moving through the air. In other words, the aspiration tube 10 is cleaned via exposure to the flow of the cleaning liquid 70, instead of immersion cleaning in which the aspiration tube 10 is immersed in an accumulated or stored cleaning liquid. During the cleaning, the discharging position of the cleaning liquid discharger 20 may be moved relative to the aspiration tube 10, or the discharging direction may be changed. In step S2, the aspiration tube 10 is moved while the cleaning liquid 70 is discharged onto the outer side surface of the aspiration tube 10 in the above-described manner.

As illustrated in FIG. 1B, the cleaning liquid 70 gets attached to the aspiration tube 10 due to the contact between the aspiration tube 10 and the cleaning liquid 70. Due to the effect of gravity, the cleaning liquid 70 attached to the aspiration tube 10 moves to and converges at the tip 11 of the aspiration tube 10, thereby forming a droplet DL.

Figure 1C:
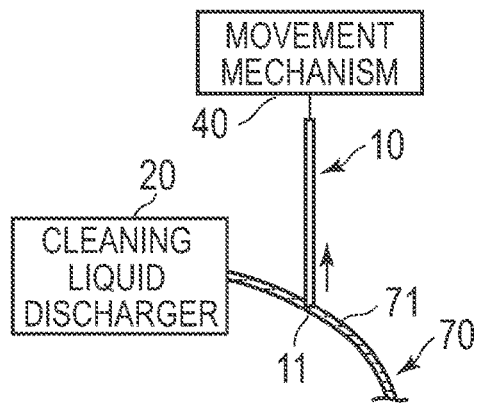
Figure 1D:
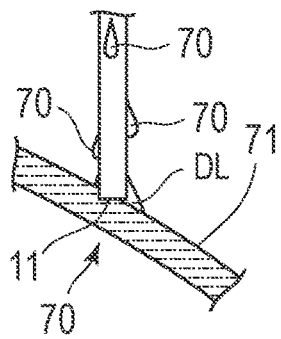

Thus, in step S3, the aspiration tube 10 is stopped in a state where the tip 11 of the aspiration tube 10 or the droplet DL attached to the tip 11 contacts the surface 71 of the flow of the cleaning liquid 70. FIGS. 1C and 1D illustrate an example in which the aspiration tube 10 is stopped in the state where the tip 11 of the aspiration tube 10 contacts the surface 71 of the flow of the cleaning liquid 70. As illustrated in FIG. 1D, while the aspiration tube 10 is stopped, the cleaning liquid 70 attached to the outer side surface of the aspiration tube 10 converges to the tip 11 along the outer side surface of the aspiration tube 10 to thereby form the droplet DL. The cleaning liquid 70 having converged at the tip 11 of the aspiration tube 10, or the droplet DL, gets combined with the flowing cleaning liquid 70, gets separated from the tip 11 by the effect of surface tension and the like, and flows away. As a result, the cleaning liquid 70, or the droplet DL, attached to the outer side surface of the aspiration tube 10 is removed from the aspiration tube 10.

Figure 1E:
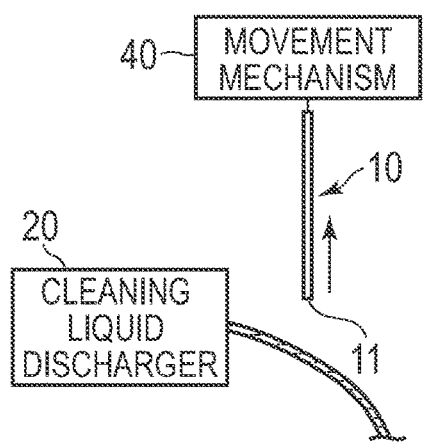
Figure 1F:
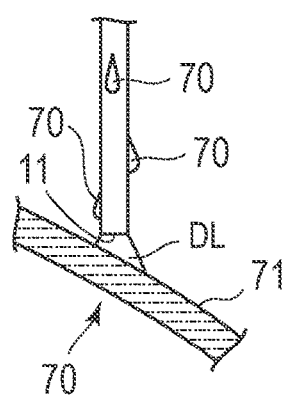

Note that an operation as illustrated in FIG. 1F may be performed instead of the operation in FIG. 1C and FIG. 1D. Specifically, FIG. 1C and FIG. 1D illustrates an example in which the aspiration tube 10 is stopped in the state where the tip 11 of the aspiration tube 10 contacts the surface 71 of the flow of the discharged cleaning liquid 70. In the example illustrated in FIG. 1F, the aspiration tube 10 is stopped in the state where the droplet DL attached to the tip 11 of the aspiration tube 10 contacts the surface 71. That is, in FIG. 1F, the tip 11 is separated from the surface 71 of the flow of the cleaning liquid 70, and only the droplet DL contacts the surface 71.

More specifically, the upward movement of the aspiration tube 10 is stopped after the tip 11 of the aspiration tube 10 is moved past the flow of the discharged cleaning liquid 70 upward. That is, the aspiration tube 10 is moved from a position where the tip 11 is under the flow of the cleaning liquid 70 through a position where the tip 11 directly contacts the flow of the cleaning liquid 70 to a position where the tip 11 is above and separated from the flow of the cleaning liquid 70. In still other words, by being moved in a direction crossing the direction of the flow of the cleaning liquid 70, the tip 11 is moved from a first position where the tip 11 does not contact the cleaning liquid 70 through a position where the tip 11 contacts the cleaning liquid 70 to a second position on the opposite side from the first position where the tip 11 does not contact the cleaning liquid 70. The aspiration tube 10 is stopped in a state where the droplet DL, which attaches to the aspiration tube 10 and converges at the tip 11, contacts the surface 71 of the flow of the cleaning liquid 70. Therefore, the cleaning liquid attached to the aspiration tube 10 gets combined with the flowing cleaning liquid 70, gets separated from the tip 11 by the effect of surface tension and the like, and flows away.

Alternatively, instead of stopping the aspiration tube 10 at the position where the tip 11 of the aspiration tube 10 (see FIG. 1D) or the droplet DL attached to the tip 11 (see FIG. 1F) contacts the surface 71 of the flow of the cleaning liquid 70, the movement of the aspiration tube 10 may be decelerated immediately before that position to create a state where the surface 71 of the flow of the cleaning liquid 70 and the droplet DL contact each other for a longer time. In this way too, the droplet DL of the cleaning liquid 70 having converted to the tip 11 along the aspiration tube 10 moves from the tip 11 side to the cleaning liquid 70 side with the surface tension of the cleaning liquid 70.

Step S3 is performed, for example, at the end of the cleaning operation on the aspiration tube 10. The end of the cleaning operation is the last moment for the aspiration tube 10 to be in contact with the cleaning liquid 70 in a single cleaning process.

Then in step S4, the stopped aspiration tube 10 is moved in a direction away from the surface 71 of the flow of the cleaning liquid 70, as illustrated in FIG. 1E. In the example of FIG. 1E, the aspiration tube 10 is moved to a position away from and above the flow of the cleaning liquid 70. As a result, the tip 11 of the aspiration tube 10 gets separated from the flow of the cleaning liquid 70, so that the removal of the droplet DL from the tip 11 of the aspiration tube 10 is completed. The discharge of the cleaning liquid 70 is then stopped. This ends the cleaning of the aspiration tube 10. Since the droplet DL is removed from the tip 11 of the aspiration tube 10, the droplet DL of the cleaning liquid 70 attached during the cleaning is prevented from being mixed into a sample or the reagent in the next dispensing of the liquid.

As described above, in the method of cleaning the aspiration tube 10 in an embodiment, the aspiration tube 10 is stopped in the state where the tip 11 of the aspiration tube 10 or the droplet DL attached to the tip 11 contacts the surface 71 of the flow of the cleaning liquid 70. Thus, while the aspiration tube 10 is stopped, the cleaning liquid 70 attached to the outer side surface of the aspiration tube 10 converges to the tip 11 along the outer side surface of the aspiration tube 10 to thereby form the droplet DL at the tip 11, and the droplet DL is moved from the tip 11 side to the cleaning liquid 70 side by the surface tension of the cleaning liquid 70. This prevents the droplet DL from remaining at the tip 11 of the aspiration tube 10, which is to dispense a sample or the reagent, after the cleaning of the aspiration tube 10.

Also, in the example of FIGS. 1A to 1F, the aspiration tube 10 is moved vertically. The aspiration tube 10 is moved upward while the cleaning liquid 70 is discharged onto the outer side surface of the aspiration tube 10, and the aspiration tube 10 is stopped in the state where the tip 11 of the aspiration tube 10 or the droplet DL attached to the tip 11 contacts the surface 71 of the flow of the cleaning liquid 70. This configuration enables removal of the droplet DL attached to the tip 11 of the aspiration tube 10 with a minimum operation involving only moving the aspiration tube 10 upward at the end of the operation of cleaning the outer side surface of the aspiration tube 10.

(Alternative Embodiment of Method of Cleaning Aspiration tube)

As illustrated in FIG. 2, the method of cleaning an aspiration tube in an alternative embodiment includes steps S1 to S4. Specifically, the method of cleaning an aspiration tube in an alternative embodiment includes steps of: (S1) obtaining position information 63 on a position of the aspiration tube 10 at which the tip 11 of the aspiration tube 10 or the droplet DL attached to the tip 11 contacts the surface 71 of the flow of the cleaning liquid 70, before discharge of the cleaning liquid 70 onto the outer side surface of the aspiration tube 10; (S2) moving the aspiration tube 10 while discharging the cleaning liquid 70 onto the outer side surface of the aspiration tube 10; (S3) decelerating or stopping the aspiration tube 10 based on the position information 63; and (S4) moving the decelerated or stopped aspiration tube 10 in a direction away from the surface 71 of the flow of the cleaning liquid 70.

In an alternative embodiment, in step S1, information on the position of the aspiration tube 10 illustrated in FIG. 1C or 1F, at which the tip 11 of the aspiration tube 10 or the droplet DL attached to the tip 11 contacts the surface 71 of the flow of the cleaning liquid 70, is obtained before the discharge of the cleaning liquid 70 onto the outer side surface of the aspiration tube 10. That is, in the example of FIG. 1C, the position of the aspiration tube 10 at the time when the tip 11 of the aspiration tube 10 contacts the surface 71 of the flow of the cleaning liquid 70 is detected before the cleaning of the aspiration tube 10. In the example of FIG. 1F, obtained is information on the position of the aspiration tube 10 at which the droplet DL attached to the tip 11 of the aspiration tube 10 contacts the surface 71 of the flow of the cleaning liquid 70. The position information is information such as a position coordinate for controlling the movement mechanism 40 or the distance of movement from a reference position of the movement mechanism 40. A method of obtaining the position information is described later in detail.

In an alternative embodiment, after the position information is obtained, in step S2, the aspiration tube 10 is moved while the cleaning liquid 70 is discharged onto the outer side surface of the aspiration tube 10 to thereby clean the aspiration tube 10. Then, in an alternative embodiment, in step S3, the aspiration tube 10 is decelerated or stopped based on the position information obtained in step S1. In the example of FIG. 1C, the aspiration tube 10 is moved to the position specified by the position information at which the tip 11 of the aspiration tube 10 contacts the surface 71 of the flow of the cleaning liquid 70. In the example of FIG. 1F, the aspiration tube 10 is moved to the position specified by the position information at which the droplet DL attached to the tip 11 of the aspiration tube 10 contacts the surface 71 of the flow of the cleaning liquid 70. Since the aspiration tube 10 is decelerated or stopped at the position specified by the position information, the state where the tip 11 of the aspiration tube 10 or the droplet DL attached to the tip 11 of the aspiration tube 10 contacts the surface 71 of the flow of the discharged cleaning liquid 70 is created in step S3. As a result, the droplet DL formed by the cleaning liquid 70 converging to the tip 11 along the aspiration tube 10 moves from the tip 11 to the flow of the cleaning liquid 70. In step S4, the decelerated or stopped aspiration tube 10 is moved in a direction away from the surface 71 of the flow of the cleaning liquid 70.

As described above, in an alternative embodiment, based on the position information 63, the aspiration tube 10 is accurately moved to the position at which the tip 11 of the aspiration tube 10 or the droplet DL attached to the tip 11 contacts the surface 71 of the flow of the cleaning liquid 70. Then, while the aspiration tube 10 is decelerated or stopped based on the position information 63, the cleaning liquid 70 attached to the outer side surface of the aspiration tube 10 converges to the tip 11 along the outer side surface of the aspiration tube 10 to thereby form the droplet DL at the tip 11, and the droplet DL is moved from the tip 11 side to the cleaning liquid 70 side by the surface tension of the cleaning liquid 70. This prevents the droplet DL from remaining at the tip 11 of the aspiration tube 10, which is to dispense a sample or the reagent, after the cleaning of the aspiration tube 10.

[Overview of Specimen Measuring Apparatus]

Next, an overview of a specimen measuring apparatus 100 is described with reference to FIG. 3.

The specimen measuring apparatus 100 is an apparatus that measures a measurement specimen prepared by adding a predetermined reagent to a sample collected from a subject.

The specimen measuring apparatus 100 detects a predetermined target component contained in the sample. The target component may contain, for example, a predetermined component, cell, or formed component in a blood or urine sample. The target component may be a nucleic acid such as DNA (deoxyribonucleic acid), a cell and an intercellular substance, an antigen or an antibody, a protein, a peptide, or the like. The specimen measuring apparatus 100 may be an immunoassay apparatus, a blood cell counter, a blood coagulation measuring apparatus, a urinary particle measuring apparatus, or the like. Alternatively, the specimen measuring apparatus 100 may be a measurement apparatus other than these.

In one example, the specimen measuring apparatus 100 is an immunoassay apparatus that detects a test substance in a sample by utilizing an antigen-antibody reaction. The immunoassay apparatus detects, for example, an antigen or an antibody, a protein, a peptide, or the like contained in the blood as a target component. The immunoassay apparatus obtains serum or plasma as a sample and performs quantitative measurement or qualitative measurement on the antigen, the antibody, or the like contained in the sample. Note that the antigen-antibody reaction includes a reaction using a specific binding substance such as an aptamer as well as the reaction between the antigen and the antibody. The aptamer is a nucleic acid molecule or a peptide synthesized so as to specifically bind to a particular substance.

The specimen measuring apparatus 100 prepares a measurement specimen by adding at least one predetermined type of reagent to a sample. As illustrated in FIG. 3, the specimen measuring apparatus 100 includes a measurement unit 30, the aspiration tube 10, the movement mechanism 40, a cleaning mechanism 50, and a controller 60.

The measurement unit 30 is configured to measure a specimen prepared to contain a sample and the reagent. Specifically, the measurement unit 30 measures a measurement specimen obtained by adding the reagent to a sample to detect a component contained in the sample. The method of detection of a target component by the measurement unit 30 is not particularly limited. It is possible to employ a method suitable for the target component, such as a chemical method, an optical method, or an electromagnetic method. The presence of the target component, the number or amount of the target component, the concentration and abundance ratio of the target component, and so on are analyzed based on the result of the detection by the measurement unit 30, for example.

The aspiration tube 10 aspirates and discharges a liquid in order to prepare a measurement specimen. The aspiration tube 10 is configured to aspirate at least one of a sample or the reagent, such as at least one of: a sample; and the reagent. The configuration of the aspiration tube 10 is as described above. The specimen measuring apparatus 100 includes at least one aspiration tube 10 or one or more aspiration tube(s) 10. The specimen measuring apparatus 100 may separately include an aspiration tube 10 for dispensing a sample and an aspiration tube 10 for dispensing the reagent. The aspiration tube 10 aspirates a sample or the reagent from the sample container 91 or the reagent container 92 and discharges the aspirated liquid into the reaction container 93. In an example, the measurement unit 30 performs measurement on a measurement specimen in the reaction container 93 prepared by dispensing the sample and the reagent. When the measurement unit 30 includes an opening to receive liquid, the aspiration tube 10 discharges the aspirated liquid into the opening of the measurement unit 30.

The movement mechanism 40 is configured to move the aspiration tube 10. The movement mechanism 40 moves the aspiration tube 10 vertically, for example. The movement mechanism 40 moves the aspiration tube 10 horizontally, for example. In an example, the movement mechanism 40 can be a mechanism for movement along two axes including one axis along the vertical direction and one axis along a predetermined horizontal direction. In an example, the movement mechanism 40 can be a mechanism for movement along three axes including one axis along the vertical direction and two axes along two orthogonal horizontal directions. The movement mechanism 40 holds the aspiration tube 10. The movement mechanism 40 holds the aspiration tube 10 such that the tip 11, in which an opening is formed for aspirating and discharging liquid, is positioned at the lowermost position. In an example, the movement mechanism 40 moves the aspiration tube 10 downward relative to a container storing a liquid from above the container to thereby bring the tip 11 into contact with the liquid. Thus, the aspiration tube 10 aspirates the liquid from the opening of the tip 11. The movement mechanism 40 moves the aspiration tube 10 to a liquid aspirating position, a liquid discharging position, and a cleaning position set in the specimen measuring apparatus 100. The aspirating position is the position where the sample container 91 or the reagent container 92 is provided. The discharging position is the position where the reaction container 93 is provided. The cleaning position is the position where the cleaning mechanism 50 is provided.

The cleaning mechanism 50 includes the cleaning liquid discharger 20, which discharges the cleaning liquid 70 for cleaning the aspiration tube 10. The cleaning liquid discharger 20 has an opening through which to discharge the cleaning liquid 70. The cleaning liquid discharger 20 is connected to a fluid circuit through which to supply the cleaning liquid 70 and discharges the cleaning liquid 70 supplied from the fluid circuit from the opening. The cleaning mechanism 50 can include a structure that receives the discharged cleaning liquid 70 and a structure that drains waste liquid being the received cleaning liquid 70 as well as the cleaning liquid discharger 20.

The controller 60 controls the operations of components of the specimen measuring apparatus 100. The controller 60 controls the measurement operation of the measurement unit 30, the movement of the aspiration tube 10 by the movement mechanism 40, the dispensing operation of the aspiration tube 10, and the discharge of the cleaning liquid 70 by the cleaning mechanism 50. The controller 60 is a processor and executes a control program.

In an embodiment, in the cleaning of the aspiration tube 10, the controller 60 controls the movement mechanism 40 so as to move the aspiration tube 10 while causing the cleaning liquid discharger 20 to discharge the cleaning liquid 70 onto the outer side surface of the aspiration tube 10, stop the aspiration tube 10 in the state where the tip 11 of the aspiration tube 10 or the droplet DL attached to the tip 11 contacts the surface 71 of the flow of the cleaning liquid 70, and move the stopped aspiration tube 10 in a direction away from the surface 71 of the flow of the cleaning liquid 70. In short, the controller 60 controls the movement mechanism 40 so as to execute the method of cleaning the aspiration tube 10 illustrated in FIGS. 1A to 1F and steps S2 to S4 in FIG. 2.

Thus, by executing the above method of cleaning the aspiration tube 10 (i.e., steps S2 to S4), the specimen measuring apparatus 100 in an embodiment prevents the droplet DL from remaining at the tip 11 of the aspiration tube 10, which is to dispense a sample or the reagent, after the cleaning of the aspiration tube 10.

(Alternative Embodiment of Specimen Measuring Apparatus)

The specimen measuring apparatus 100 according to an alternative embodiment is configured to execute the method of cleaning an aspiration tube including steps 51 to S4 illustrated in FIG. 2. Specifically, the specimen measuring apparatus 100 in an alternative embodiment includes a liquid surface detector 65 illustrated by the long dashed double-short dashed line in FIG. 3. The liquid surface detector 65 detects contact of the tip 11 of the aspiration tube 10 or the droplet DL attached to the tip 11 with the surface 71 of the flow of the cleaning liquid 70.

Then, before the discharge of the cleaning liquid 70 onto the outer side surface of the aspiration tube 10 from the cleaning liquid discharger 20, the controller 60 of the specimen measuring apparatus 100 according to an alternative embodiment obtains the position information 63 on the position of the aspiration tube 10 at which the tip 11 of the aspiration tube 10 or the droplet DL attached to the tip 11 contacts the surface 71 of the flow of the cleaning liquid 70, based on the result of the detection by the liquid surface detector 65. The controller 60 then controls the movement mechanism 40 so as to move the aspiration tube 10 while causing the cleaning liquid discharger 20 to discharge the cleaning liquid 70 onto the outer side surface of the aspiration tube 10, decelerate or stop the aspiration tube 10 based on the position information 63, and move the decelerated or stopped aspiration tube 10 in a direction away from the surface 71 of the flow of the cleaning liquid 70. In short, the controller 60 controls the movement mechanism 40 so as to execute the method of cleaning the aspiration tube 10 illustrated in FIG. 1 and steps S1 to S4 in FIG. 2.

Thus, by executing the above method of cleaning the aspiration tube 10 (i.e., steps S1 to S4) according to an alternative embodiment, the specimen measuring apparatus 100 in an alternative embodiment prevents the droplet DL from remaining at the tip 11 of the aspiration tube 10, which is to dispense a sample or the reagent, after the cleaning of the aspiration tube 10.

(Examples of Change in Movement Speed at Time of Contact with Surface of Flow of Cleaning Liquid)

In the method of cleaning the aspiration tube 10 illustrated in FIGS. 1A to 1F, the aspiration tube 10 is stopped at the position illustrated in FIG. 1C, at which the tip 11 contacts the surface 71 of the flow of the cleaning liquid 70, or the position illustrated in FIG. 1F, at which the droplet DL attached to the tip 11 of the aspiration tube 10 contacts the surface 71 of the flow of the cleaning liquid 70. It takes only a short time for the droplet DL to be removed by contacting the surface 71 of the flow of the cleaning liquid 70. Thus, the time for which to stop the aspiration tube 10 only needs to be a short time and may be 0.1 second or longer and 1 second or shorter, for example.

In a modification of the method of cleaning the aspiration tube 10, the movement of the aspiration tube 10 may be decelerated immediately before the position illustrated in FIG. 1C, at which the tip 11 contacts the surface 71, or the position illustrated in FIG. 1F, at which the droplet DL attached to the tip 11 contacts the surface 71. In an example, the controller 60 decelerates the movement to a movement speed lower than the movement speed of the aspiration tube 10 in the cleaning operation in which the aspiration tube 10 is brought into contact with the cleaning liquid 70. The controller 60 positions the aspiration tube 10 at the position at which the tip 11 contacts the surface 71 or the position at which the droplet DL attached to the tip 11 contacts the surface 71 while the aspiration tube 10 is in the decelerated state. When the aspiration tube 10 is positioned at the position at which the tip 11 contacts the surface 71 or the position at which the droplet DL attached to the tip 11 contacts the surface 71, the movement speed of the aspiration tube 10 may be in the process of being continuously or gradually lowered or in the process of being maintained constant at a decelerated speed. Once reaching the position at which the tip 11 contacts the surface 71 or the position at which the droplet DL attached to the tip 11 contacts the surface 71, the aspiration tube 10 may be stopped or moved in a direction away from the flow of the cleaning liquid 70 without being stopped.

(Modifications of Discharge of Cleaning Liquid)

Figure 4A:
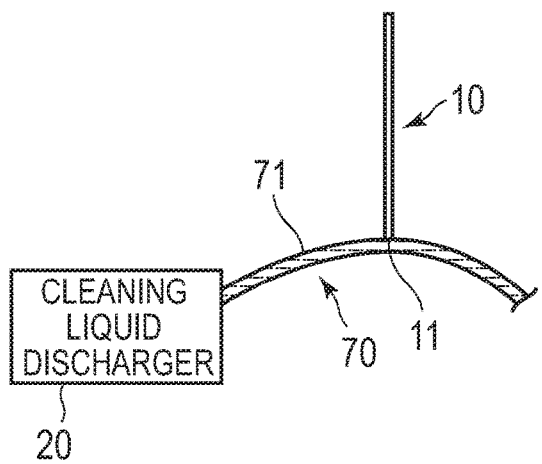
FIGS. 4A and 4B are schematic diagrams illustrating examples of a positional relation between an aspiration tube and a cleaning liquid discharged from a cleaning liquid discharger.

Although FIGS. 1A to 1F illustrate an example in which the cleaning liquid discharger 20 discharges the cleaning liquid 70 in a lateral direction (horizontal direction), the discharging direction is not limited to this. In FIG. 4A, the cleaning liquid discharger 20 discharges the cleaning liquid 70 obliquely upward. In an example, the aspiration tube 10 is arranged along the vertical direction and is moved such that the tip 11 contacts the surface 71 of the flow of the cleaning liquid 70 around the top, or the highest point, of the flow of the cleaning liquid 70.

Figure 4B:
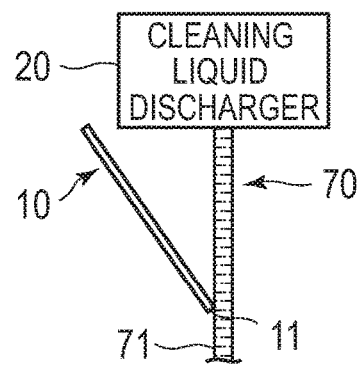

In FIG. 4B, the cleaning liquid discharger 20 discharges the cleaning liquid 70 downward. In an example, the aspiration tube 10 is arranged along a direction inclined obliquely downward and is laterally moved toward the flow of the cleaning liquid 70 such that the tip 11 contacts the surface 71 of the flow of the cleaning liquid 70.

(Directions of Movements to Surface of Flow of Cleaning Liquid)

In the method of cleaning the aspiration tube 10 in the example illustrated in FIGS. 1A to 1E, a portion of the aspiration tube 10 above the tip 11 is brought into contact with the flow of the cleaning liquid 70 to thereby be cleaned (see FIG. 1B), the aspiration tube 10 is moved upward with the cleaning liquid 70 in contact with the aspiration tube 10, and the aspiration tube 10 is positioned at the position at which the tip 11 contacts the surface 71 of the flow of the cleaning liquid 70 (see FIG. 1C). In short, the portion above the tip 11 is brought into contact with the flow of the cleaning liquid 70 to thereby be cleaned, and the aspiration tube 10 in that state is moved upward so as to bring the tip 11 into contact with the surface 71 of the flow of the cleaning liquid 70.

Figure 5A:
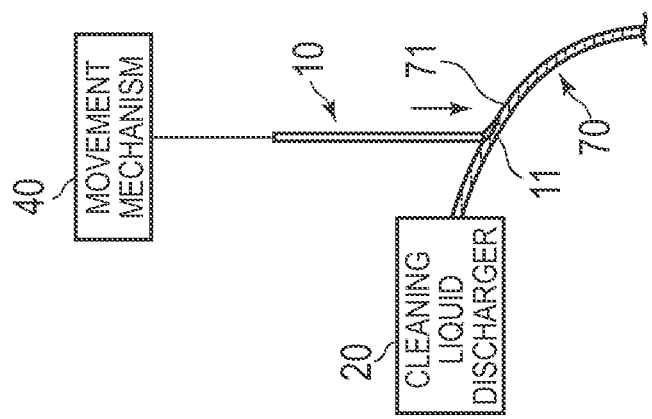
FIGS. 5A to 5C are schematic diagrams illustrating an operation example in which a tip of an aspiration tube is caused to approach a surface of a flow of a cleaning liquid from above.
Figure 5B:
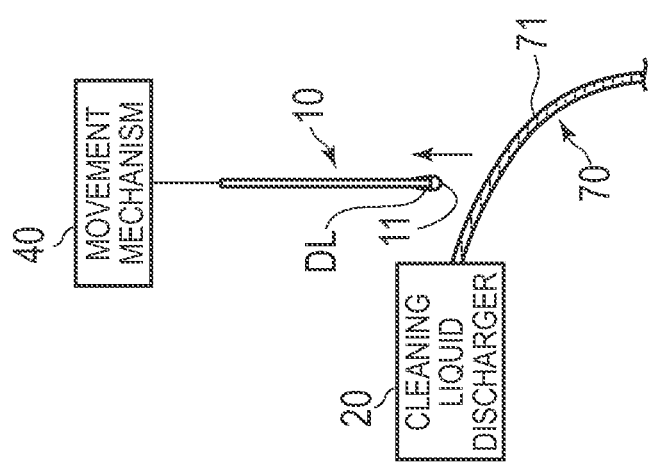
Figure 5C:
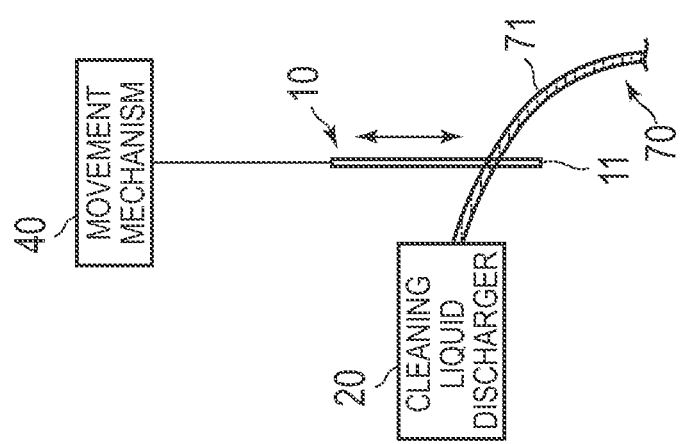

In FIGS. 5A to 5C, the portion of the aspiration tube 10 above the tip 11 is brought into contact with the flow of the cleaning liquid 70 to thereby be cleaned (see FIG. 5A), the aspiration tube 10 is moved upward to an upper position at which the tip 11 of the aspiration tube 10 does not contact the flow of the cleaning liquid 70 (see FIG. 5B), and then the tip 11 is moved downward to a position below the flow of the cleaning liquid 70 (see FIG. 5C). Thereafter, when moved upward again, the aspiration tube 10 may be stopped at the position illustrated in FIG. 1C, at which the tip 11 contacts the surface 71 of the flow of the cleaning liquid 70, or the position illustrated in FIG. 1 F, at which the droplet DL attached to the tip 11 of the aspiration tube 10 contacts the surface 71 of the flow of the cleaning liquid 70.

(Examples of Specimen Measuring Apparatus)

Examples of the specimen measuring apparatus 100 are described. In an example, the specimen measuring apparatus 100 is an immunoassay apparatus.

(Immunoassay)

The specimen measuring apparatus 100 that performs an immunoassay measures light that is generated from a specimen, specifically, chemiluminescent light that is based on a test substance contained in a sample. The specimen measuring apparatus 100 generates measurement data based on the light detected by a detector included in the measurement unit 30. The detector can include, for example, an image capture unit including an image sensor or a light detector such as a photomultiplier tube, a phototube, or a photodiode.

Here, chemiluminescent light is light emitted by utilizing energy resulting from a chemical reaction. Chemiluminescent light is, for example, light emitted when a molecule brought into an excited state by being excited by a chemical reaction returns to the ground state from the excited state. The chemiluminescent light to be detected by the detector is, for example, based on a chemiluminescence enzyme immunoassay (CLEIA) and is light generated as the result of a reaction between an enzyme and a substrate.

As a chemiluminescence enzyme immunoassay, a 2-step method, for example, involves: (1) supporting a test substance in a sample onto a solid-state carrier inside a reaction container; (2) performing primary B/F separation that separates the solid-state substance supporting the test substance and a liquid-state substance; (3) binding a labeled substance to the solid-state substance supporting the test substance in the reaction container; (4) performing secondary B/F separation; and (5) causing an enzymatic reaction by adding a chemiluminescent substrate into the reaction container.

Chemiluminescence enzyme immunoassays include publicly known 1-step methods, D-1-step methods (delayed one-step methods), and so on as well as 2-step methods. HBsAg is a measurement item in a 2-step method. HBsAb is a measurement item in a 1-step method. FT3, FT4, TSH, and so on are measurement items in a D-1-step method.

Note that the chemiluminescent light to be detected by the detector may be, for example, light based on a chemiluminescence immunoassay (CLIA), an electrochemiluminescence immunoassay (ECLIA), a fluorescence enzyme immunoassay (FEIA), an LOCI (Luminescent Oxygen Channeling Immunoassay), a BLEIA (bioluminescent enzyme immunoassay), or the like.

(Blood Coagulation Analysis)

In an example, the specimen measuring apparatus 100 may be a blood coagulation analyzer that performs a blood coagulation analysis. The specimen measuring apparatus 100 that performs a blood coagulation analysis includes a detector that applies light to a measurement specimen prepared by adding a reagent to a sample and detects transmitted light or scattered light of the light applied to the measurement specimen. The sample is plasma or serum separated from blood. The specimen measuring apparatus 100 analyzes the sample by using a coagulation method, a synthetic substrate method, an immunonephelometric method, or an aggregation method.

In the coagulation method, light is applied to the measurement specimen, and the time taken for the fibrinogen in the sample to convert into fibrin is measured based on an electrical signal representing transmitted light or scattered light from the specimen. PT (prothrombin time), APTT (activated partial thromboplastin time), Fbg (fibrinogen amount), and so on are measurement item in the coagulation method.

In the synthetic substrate method, light is applied to the measurement specimen, and the degree of color development by the effect of a chromogenic synthetic substrate on an enzyme in the measurement specimen is measured based on an electrical signal representing transmitted light from the specimen. ATIII (antithrombin III), α2-PI (α2-plasmin inhibitor), PLG (plasminogen), and so on are measurement items in the synthetic substrate method.

In the immunonephelometric method, a reagent that causes antigen-antibody reactions with coagulation and fibrinolysis factors or the like in the sample is added to the sample, and substances contained in the reagent aggregate as the result of the antigen-antibody reactions. In the immunonephelometric method, light is applied to the measurement specimen, and the rates of aggregation of the substances contained in the reagent in the measurement specimen are measured based on an electrical signal representing transmitted light or scattered light from the specimen. D-dimer, FDP (fibrin degradation product), and so on are measurement items in the immunonephelometric method.

In the aggregation method, light is applied to the measurement specimen, and based on an electrical signal representing transmitted light from the specimen, the change in absorbance in the course of an aggregative reaction of platelets or the like in the measurement specimen is measured. vWF:RCo(von Willebrand Factor Ristocetin Cofactor), the platelet aggregation ability, and so on are measurement items in the aggregation method.

(Blood Cell Analysis)

Alternatively, the specimen measuring apparatus 100 may be an automated analyzer for blood cell count measurement (what is called a blood cell analyzer), for example. The specimen measuring apparatus 100 causes a measurement specimen prepared by mixing a blood sample and a reagent to flow through a flow path, and detects and counts blood cell components flowing through the flow path. The measurement unit 30 detects the blood cell components by a flow cytometry method, for example. Specifically, the detector includes a flow path unit through which the specimen is caused to flow, a light emitter which applies measurement light to the specimen flowing through the flow path unit, and a light receiver which detects the light applied to the specimen.

The detector causes particles such as cells to flow in a flow of a sheath fluid formed in the flow path unit, applies a laser beam to the flowing particles from the light emitter, and detects the resultant scattered light or fluorescence with the light receiver. The specimen measuring apparatus 100 analyzes each individual particle based on the light detected by the detector. In an example, a scatter gram in which scattered light intensity and fluorescence intensity are combined as parameters or the like is generated, and the specimen is analyzed based on the distribution in the scattergram or the like. NEUT (neutrophil), LYMPH (lymphocyte), MONO (monocyte), EO (eosinophil), BASO (basophil), and so on are measurement items in the flow cytometry method.

Alternatively, the specimen measuring apparatus 100 performs a detection by a sheath flow DC detection method, for example. Specifically, the measurement unit 30 includes a flow path unit that is provided with an opening portion through the specimen is caused to flow, and a detector that detects electrical changes between a pair of electrodes arranged to face each other with the opening portion therebetween. The detector causes particles such as cells to flow in a flow of a sheath fluid passing through the opening portion and causes a DC current to flow between the electrodes. The detector detects each individual particle based on the pulse-shaped change in current occurring when the particle passes the opening portion. WBC (white blood cell) count, RBC (red blood cell) count, HGB (hemoglobin amount), HCT (hematocrit value), MCV (mean corpuscular volume), MCH (mean corpuscular hemoglobin), MCHC (mean corpuscular hemoglobin concentration), PLT (platelet count), and so on are measurement items in the sheath flow DC detection method.

[Specific Configuration Example of Specimen Measuring Apparatus]

Next, a specific configuration example of the specimen measuring apparatus 100 is described in detail with reference to FIGS. 6 to 22. In the example of FIGS. 6 to 22, the specimen measuring apparatus 100 is an immunoassay apparatus that detects a test substance in a sample by utilizing an antigen-antibody reaction. Also, in the example of FIGS. 6 to 22, the specimen measuring apparatus 100 is connected to a blood coagulation measuring apparatus 200. That is, in the example illustrated in FIG. 6, the specimen measuring apparatus 100 as an immunoassay apparatus and the blood coagulation measuring apparatus 200 form a composite measurement system capable of measuring a sample for a number of items with different measurement principles. The specimen measuring apparatus 100 does not have to be connected to the blood coagulation measuring apparatus 200 and may be used alone.

(Configuration of Blood Coagulation Measuring Apparatus)

Figure 6:
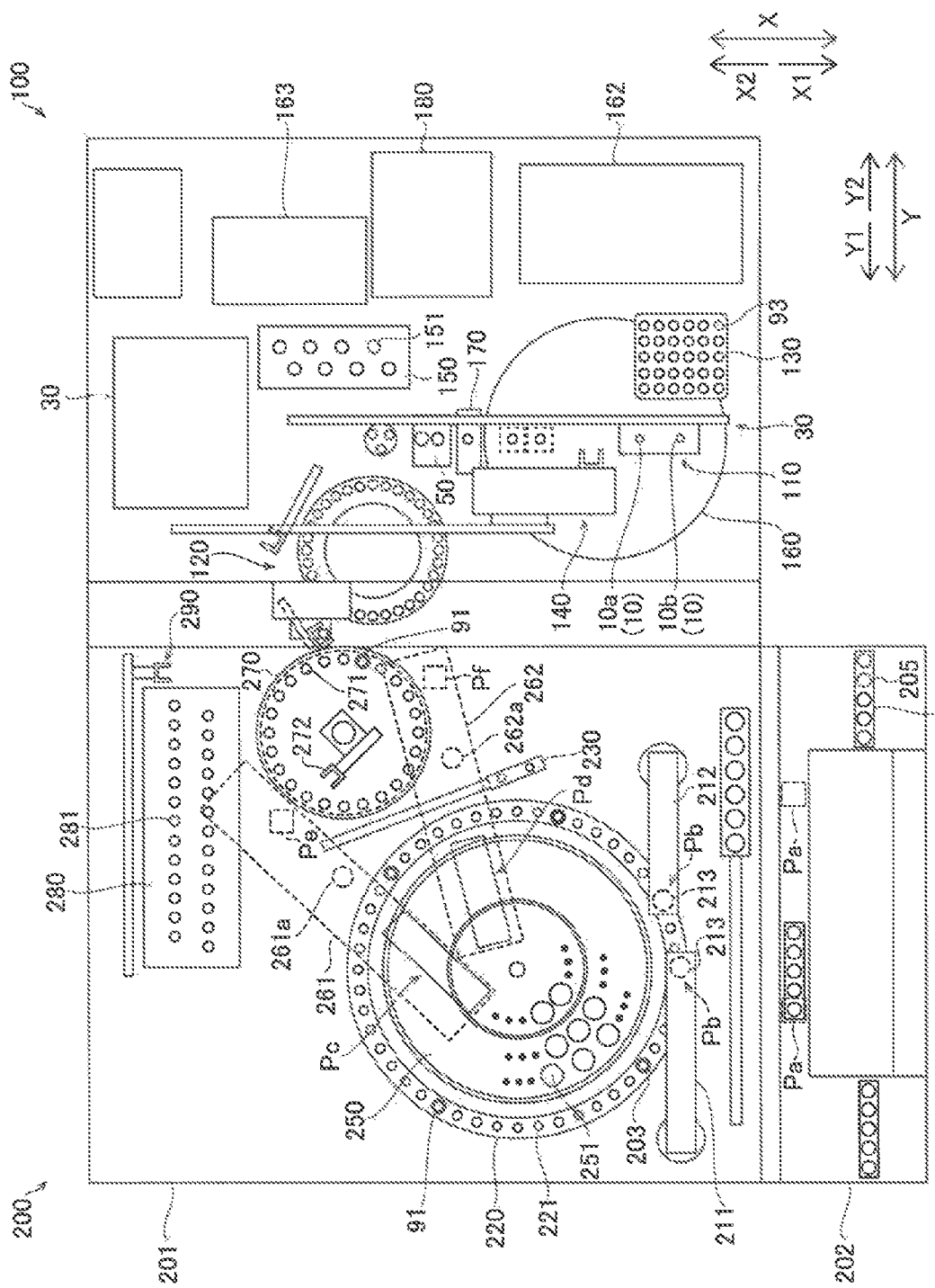
FIG. 6 is a diagram of a schematic plan view illustrating a configuration example of a specimen measuring apparatus and a blood coagulation measuring apparatus.

In the configuration example of FIG. 6, the blood coagulation measuring apparatus 200 includes a measurement mechanism unit 201 and a transporter 202.

Sample racks 204 are placed in the transporter 202. Sample containers 205 each storing a sample can be placed in each sample rack 204. The transporter 202 transports a sample rack 204 placed by the user and positions sample containers 205 at predetermined sample aspirating positions Pa in plan view. The sample container 205 is a blood collection tube, for example.

The measurement mechanism unit 201 includes sample dispensing units 211 and 212 that each aspirate the sample in a sample container 205 and dispense it in a predetermined amount into a reaction container 203 or a sample container 91.

The sample dispensing units 211 and 212 include a dispensing arm that pivotally holds an aspiration tube 213 for dispensing a sample. The sample dispensing units 211 and 212 are each capable of moving the aspiration tube 213 and aspirating a predetermined amount of a sample from a sample container 205 at the corresponding sample aspirating position Pa. The sample dispensing units 211 and 212 are each capable of moving the aspiration tube 213 and discharging the aspirated sample into a reaction container 203 or a sample container 91 positioned at a predetermined sample dispensing position Pb. The reaction container 203 and the sample container 91 are cuvettes, for example.

The measurement mechanism unit 201 includes a mechanism that stores samples and reagents and transfers reaction containers 203 in which measurement specimens are to be prepared to given sections. In the configuration example of FIG. 6, the measurement mechanism unit 201 includes a container table 220. The container table 220 has a ring shape in plan view and is capable of rotating in its circumferential direction. The container table 220 includes holding holes 221 arrayed along the circumferential direction. One reaction container 203 or sample container 91 can be placed in each holding hole 221. The sample dispensing units 211 and 212 are each capable of dispensing an aspirated sample into a new reaction container 203 held by the container table 220 at the corresponding sample dispensing position Pb in plan view. Also, the sample dispensing units 211 and 212 are each capable of aspirating a sample from a reaction container 203 on the container table 220 storing the sample.

The measurement mechanism unit 201 includes a transfer unit 230 that positions a new reaction container 203 at a sample dispensing position. The transfer unit 230 is capable of moving a placement stage along a rail, the placement stage including holding holes in which to place reaction containers 203. The sample dispensing unit 212 is capable of dispensing an aspirated sample into a new reaction container 203 held by the transfer unit 230. Each reaction container 203 is placed in a holding hole 221 of the container table 220 or a holding hole of the transfer unit 230.

The measurement mechanism unit 201 includes a reagent table 250 that stores reagent containers 251 to be used in measurement, and reagent dispensing units 261 and 262 that each aspirate a reagent from a reagent container 251 placed on the reagent table 250 and discharge the reagent.

The reagent table 250 is arranged inside the container table 220 and has a circular shape in plan view. The reagent containers 251 can be placed on the reagent table 250 along its circumferential direction. The reagent table 250 is capable of rotating in the circumferential direction and positioning any of the reagent containers 251 at predetermined reagent aspirating positions Pc and Pd in plan view via rotation.

The reagent dispensing unit 261 includes an aspiration tube 261a for dispensing a reagent. The reagent dispensing unit 262 includes an aspiration tube 262a for dispensing a reagent. The reagent dispensing units 261 and 262 are capable of aspirating predetermined amounts of reagents from reagent containers 251 on the reagent table 250 positioned at the reagent aspirating positions Pc and Pd, respectively. The reagent dispensing units 261 and 262 are capable of moving their aspiration tubes to reagent dispensing positions Pe and Pf in plan view and discharging the predetermined amounts of the reagents into reaction containers 203 at the reagent dispensing positions, respectively.

The measurement mechanism unit 201 includes a heating table 270 that holds and heats reaction containers 203 in which samples have been dispensed. The heating table 270 includes holding holes 271 in which to hold reaction containers 203 and a gripping mechanism 272 which grips and transfers a reaction container 203.

The heating table 270 has a circular shape in plan view, and the holding holes 271 are arrayed along its circumferential direction. The heating table 270 is capable of rotating in the circumferential direction and transferring the reaction containers 203 placed in the holding holes 271 in the circumferential direction via rotation. The gripping mechanism 272 is capable of gripping and transferring a reaction container 203.

The gripping mechanism 272 is capable of transferring a reaction container 203 placed on the transfer unit 230 to a holding hole 271 of the heating table 270. The gripping mechanism 272 is also capable of taking out a reaction container 203 heated in a holding hole 271 of the heating table 270 and transferring the reaction container 203 to the reagent dispensing position Pe or Pf. The gripping mechanism 272 returns a reaction container 203 in which a reagent has been dispensed by the reagent dispensing unit 261 or 262 to a holding hole 271 of the heating table 270.

The measurement mechanism unit 201 includes a detector 280 that performs optical measurement on measurement specimens in reaction containers 203. The detector 280 includes container placement parts 281 in which to place reaction containers 203 storing samples, and light reception portions which are provided respectively for the container placement parts 281.

The measurement mechanism unit 201 includes a gripping mechanism 290 that transfers a reaction container 203 to the detector 280. The gripping mechanism 290 is capable of gripping and transferring a reaction container 203 in X, Y, and Z directions being the directions of three orthogonal axes. The gripping mechanism 290 is capable of transferring a reaction container 203 from a holding hole 271 of the heating table 270 to the reagent dispensing position Pe and placing the reaction container 203 after a reagent is dispensed into a container placement part 281 of the detector 280.

The optical measurement is performed on the measurement specimens in the reaction containers 203 placed in the container placement parts 281 of the detector 280. Measurement light is applied to the reaction containers 203 placed in the container placement parts 281 of the detector 280. The detector 280 receives transmitted light or scattered light of the light applied to the reaction containers 203 and outputs electrical signals corresponding to the amounts of light received. The samples are measured based on the outputted electrical signals.

The blood coagulation measuring apparatus 200 is capable of passing a sample to the specimen measuring apparatus 100. Specifically, the blood coagulation measuring apparatus 200 transports a sample container 91 storing a sample dispensed by the sample dispensing unit 211 or 212 to the specimen measuring apparatus 100 with the gripping mechanism 272 by way of the container table 220 and the heating table 270.

(Configuration of Specimen Measuring Apparatus)

Figure 7:
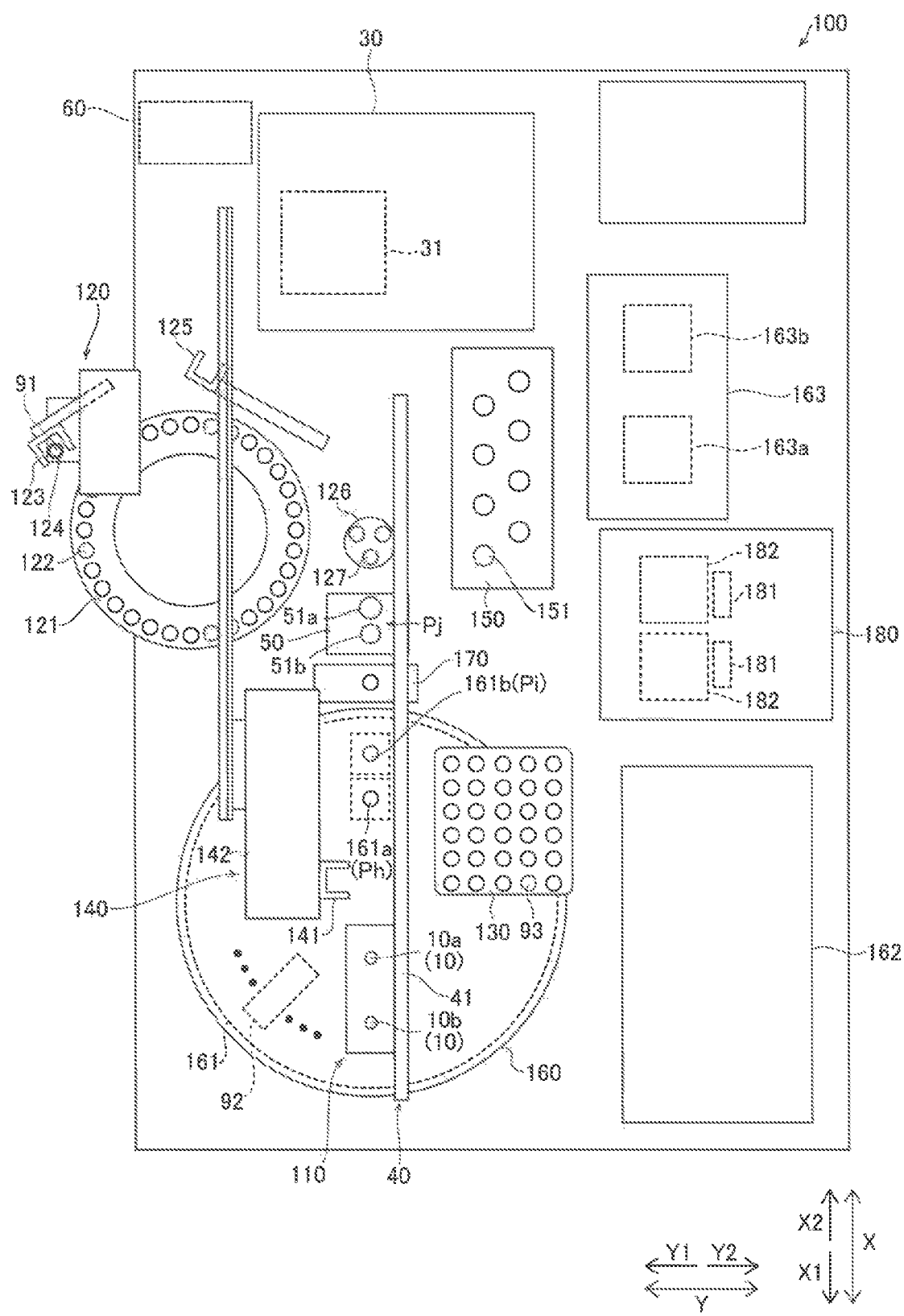
FIG. 7 is a diagram of a plan view illustrating a configuration example of a specimen measuring apparatus.

As illustrated in FIG. 7, the specimen measuring apparatus 100 includes the measurement unit 30, the controller 60, a dispensing unit 110, the movement mechanism 40, the cleaning mechanism 50, a sample transporter 120, a reaction container supply unit 130, a container transporter 140, a heater 150, a reagent storage 160, a reagent cooler 162, a reagent dispensing unit 163, a spot application unit 170, and a B/F separator 180.

The sample transporter 120 transports a sample collected from a subject to a position at which the sample is to be aspirated. The sample transporter 120 includes a reception table 121, a reception catcher 123, a reception port 124, a transporter 125, and a sample supply unit 126. The sample transporter 120 receives a sample from the blood coagulation measuring apparatus 200 and transports the received sample to the sample supply unit 126.

The reception table 121 has a ring shape in plan view and is capable of rotating in its circumferential direction. The reception table 121 is provided with holding holes 122 arrayed along the circumferential direction. One sample container 91 can be placed in each holding hole 122. The reception catcher 123 transports a sample container 91 mounted in the reception port 124 to a holding hole 122 of the reception table 121. In the reception port 124, a sample container 91 transported from the blood coagulation measuring apparatus 200 is mounted.

The transporter 125 transports a sample container 91 held in a holding hole 122 of the reception table 121 to a holding hole 127 of the sample supply unit 126. The transporter 125 also transports a reaction container 93 to be used to prepare a specimen to the measurement unit 30. In an example, the transporter 125 includes a catcher that holds a sample container 91. The reaction container 93 is a cuvette, for example.

The sample supply unit 126 has a circular shape in plan view and is capable of rotating in its circumferential direction. The sample supply unit 126 is provided with multiple (three) holding holes 127 arrayed along the circumferential direction. One sample container 91 can be placed in each holding hole 127.

The reaction container supply unit 130 holds reaction containers 93 such that the reaction containers 93 can be individually taken out.

The container transporter 140 transfers a reaction container 93. Specifically, the container transporter 140 transports a reaction container 93 along the moving direction of the dispensing unit 110. Moreover, the container transporter 140 obtains a reaction container 93 from the reaction container supply unit 130 and transfers the reaction container 93 to processing positions on the heater 150, the reagent dispensing unit 163, the spot application unit 170, the B/F separator 180, and so on. The container transporter 140 includes a catcher 141 and a container movement mechanism 142.

The catcher 141 grips a reaction container 93. The catcher 141 is also capable of swinging a reaction container 93 in the state of gripping the reaction container 93. The container movement mechanism 142 supports the catcher 141 movably in each of an up-down direction (Z direction), a left-right direction (Y direction), and a front-rear direction (X direction). Thus, the catcher 141 is movable in horizontal directions (X and Y directions) and also movable in the vertical direction (Z direction).

The heater 150 includes a heater and a temperature sensor, and holds reaction containers 93 and heats specimens stored in the reaction containers 93 to thereby react the specimens. The heater 150 heats reaction containers 93 in which liquids have been dispensed. The heater 150 is provided with holding holes 151 in each of which one reaction container 93 can be placed. The heating by the heater 150 causes a sample and a reagent stored in the reaction container 93 to react with each other.

The reagent storage 160 includes a reagent container holder 161 capable of holding reagent containers 92. The reagent container holder 161 is provided inside the reagent storage 160, which has a cylindrical shape. In the reagent storage 160 are placed reagent containers 92 storing reagents to be dispensed by the dispensing unit 110. The reagent containers 92 can be placed in the reagent container holder 161 in the circumferential direction. The reagent container holder 161 is capable of rotating in the circumferential direction and positioning any of the reagent containers 92 at a predetermined reagent aspirating position Ph or Pi in plan view via rotation. Also, the reagent storage 160 is provided with a cooling mechanism and kept cooled at a constant temperature suitable for storage of the reagents. The reagent container holder 161 holds an R1 reagent, an R2 reagent, and an R3 reagent, for example. The reagent aspirating positions Ph and Pi are located under the movement mechanism 40.

The dispensing unit 110 includes an aspiration tube 10*a* for dispensing a sample and an aspiration tube 10*b* for dispensing a reagent. The aspiration tube 10*a* and the aspiration tube 10*b* are arranged next to each other along the X direction with a gap therebetween. The movement mechanism 40 supports and moves the dispensing unit 110. The movement mechanism 40 moves the dispensing unit 110, which includes the aspiration tube 10*a* and the aspiration tube 10*b*, together with them. The movement mechanism 40 is capable of moving the dispensing unit 110 linearly along the X direction within a horizontal plane.

The reagent cooler 162 cools an R4 reagent and an R5 reagent. The reagent cooler 162 cools the R4 reagent and the R5 reagent at a constant temperature suitable for storage. The reagent dispensing unit 163 is fluidly connected to the reagent cooler 162 and dispenses the R4 reagent and the R5 reagent into a reaction container 93. The reagent dispensing unit 163 includes an R4 reagent dispensing unit 163*a* and an R5 reagent dispensing unit 163*b*. The R4 reagent dispensing unit 163*a* dispenses the R4 reagent into a reaction container 93 transferred by the container transporter 140. The R5 reagent dispensing unit 163*b* dispenses the R5 reagent into a reaction container 93 transferred by the container transporter 140.

The cleaning mechanism 50 cleans the aspiration tube 10*a* and the aspiration tube 10*b* by using the cleaning liquid 70. The cleaning mechanism 50 is placed at a cleaning position Pj directly under a path along which the aspiration tube 10*a* and the aspiration tube 10*b* are moved by the movement mechanism 40. Each time an aspiration tube 10, among the aspiration tube 10*a* and the aspiration tube 10*b*, aspirates a liquid, the cleaning mechanism 50 cleans the aspiration tube 10 that has aspirated the liquid with the cleaning liquid. Also, the cleaning mechanism 50 sequentially cleans the aspiration tube 10*a* and the aspiration tube 10*b* in an initial operation and a termination operation of the specimen measuring apparatus 100.

The spot application unit 170 is capable of holding a reaction container 93 movably in the vertical direction (Z direction). At the spot application unit 170, a sample is dispensed via spot application into the reaction container 93 by the aspiration tube 10*a*. The R1 reagent also is dispensed by the aspiration tube 10*b* at the spot application unit 170.

The B/F separator 180 has a function of executing B/F separation processes (see FIG. 22) that separate a liquid-phase substance and a solid-phase substance from each other in a reaction container 93. The B/F separator 180 includes one or more processing ports in each of which a reaction container 93 can be placed. Each processing port is provided with a magnetic source 181 that magnetically attracts magnetic particles contained in the R2 reagent, and a cleaning unit 182 that aspirates the liquid-phase substance and supplies a cleaning liquid. With the cleaning unit 182, the B/F separator 180 aspirates the liquid-phase substance in the reaction container 93 and supplies the cleaning liquid into it in a state where each magnetic particle with an immune complex formed thereon is magnetically attracted. This enables separation and removal of unnecessary components contained in the liquid-phase substance from the bound bodies of the immune complex and the magnetic particle.

The measurement unit 30 includes a light detector 31, such as a photomultiplier tube. With the light detector 31, the measurement unit 30 obtains light generated in the course of a reaction between a labeled antibody binding to an antigen in a sample after various processes and a luminescent substrate to measure the amount of the antigen contained in the sample. The measurement unit 30 measures a sample heated by the heater 150. Also, the measurement unit 30 measures a sample on which the B/F separation processes have been performed by the B/F separator 180.

(Movement Mechanism)

Figure 8:
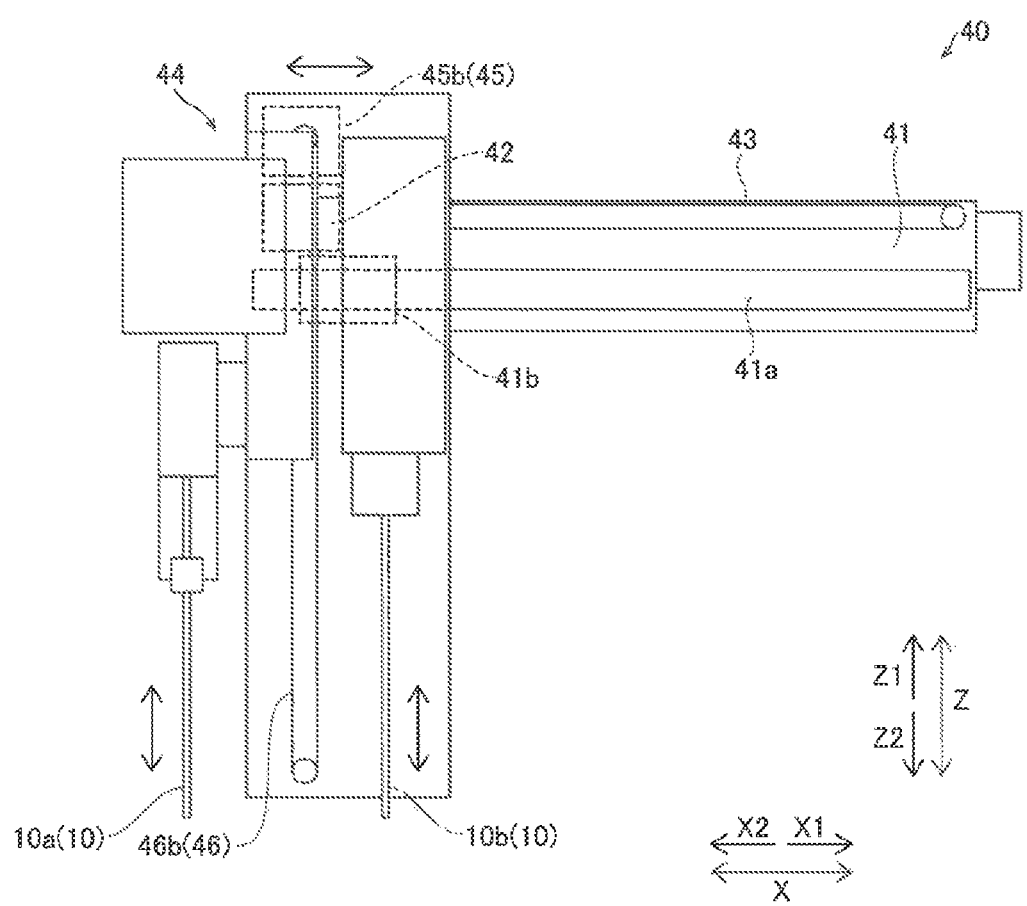
FIG. 8 is a diagram of a side view illustrating a movement mechanism.
Figure 9:
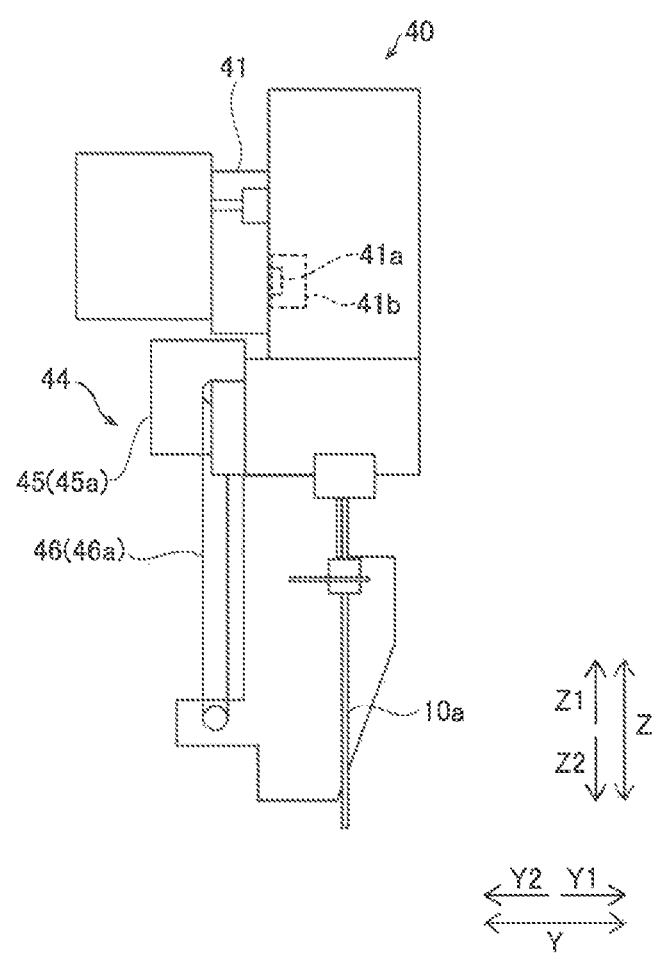
FIG. 9 is a diagram of a back view illustrating a movement mechanism.

As illustrated in FIGS. 8 and 9, the movement mechanism 40 includes a support 41, a rail 41a, a mover 41b, a motor 42, and a belt mechanism 43. The support 41 supports both the aspiration tube 10a and the aspiration tube 10b movably. The support 41 is shared by the aspiration tube 10a and the aspiration tube 10b. Note that each of the aspiration tube 10a and the aspiration tube 10b may be individually supported. Moreover, each of the aspiration tube 10a and the aspiration tube 10b may be moved independently of each other in the direction of one axis.

The support 41 is formed in a plate shape extending along the X direction and the Z direction. Both the aspiration tube 10a and the aspiration tube 10b are provided on a plate-shaped side face of the support 41 on one side (the side face on a Y1 side). The rail 41a is provided on the support 41 so as to extend in the X direction. The mover 41b is coupled to the rail 41a. The mover 41b is guided by the rail 41a to move in the X direction along the support 41. In an example, the mover 41b is a slider that moves along the rail 41a.

The motor 42 is configured to drive the belt mechanism 43. In an example, the motor 42 is a stepping motor and is driven by pulse signals outputted from the controller 60. The belt mechanism 43 includes a belt and pulleys and is connected to the dispensing unit 110, which includes the aspiration tube 10a and the aspiration tube 10b. Movement of the belt of the belt mechanism 43 moves the connected dispensing unit 110 in the X direction.

The movement mechanism 40 includes a vertical mover 44. The vertical mover 44 vertically moves the aspiration tube 10a and the aspiration tube 10b independently of each other. This enables the aspiration tube 10a and the aspiration tube 10b to aspirate and discharge a liquid independently of each other. The vertical mover 44 includes a motor 45 and a belt mechanism 46 for each aspiration tube 10. Specifically, the vertical mover 44 includes a motor 45a and a belt mechanism 46a (see FIG. 9) that vertically move the aspiration tube 10a, and a motor 45b and a belt mechanism 46b (see FIG. 8) that vertically move the aspiration tube 10b.

The motor 45 (45a, 45b) and the belt mechanism 46 (46a, 46b) vertically move the aspiration tube 10a or the aspiration tube 10b. The motor 45 and the belt mechanism 46 are moved in the direction of one axis (X direction) along with the aspiration tube 10a or the aspiration tube 10b. The motor 45 is configured to drive the belt mechanism 46. In an example, the motor 45 is a stepping motor and is driven by pulse signals from the controller 60. The belt mechanism 46 includes a belt and pulleys and is connected to either the aspiration tube 10a or the aspiration tube 10b. Movement of the belt of the belt mechanism 46 moves the connected aspiration tube 10a or aspiration tube 10b in the vertical direction (Z direction). Note that the upper limit positions in the ranges of vertical movement of the aspiration tube 10a and the aspiration tube 10b are set as the home positions of the respective motors 45. The vertical positions of the aspiration tube 10a and the aspiration tube 10b are controlled based on the numbers of pulses from the respective home positions.

(Dispensing Unit)

The dispensing unit 110 includes the aspiration tube 10a and the aspiration tube 10b. The aspiration tube 10a is configured to aspirate and discharge a sample. The aspiration tube 10b is configured to aspirate and discharge a reagent. The aspiration tube 10b is configured to aspirate and discharge multiple types of reagents. Specifically, the aspiration tube 10b is configured to aspirate and discharge the R1 reagent, the R2 reagent, and the R3 reagent.

The dispensing unit 110 holds the aspiration tube 10a on a first side in the X direction (X2 direction side) and holds the aspiration tube 10b on a second side in the X direction (X1 direction side), which is opposite from the first side. The aspiration tube 10a aspirates a sample from a sample container 91 transported by the transporter 125 and storing the sample. The aspiration tube 10b aspirates the reagents from the reagent containers 92 placed in the reagent storage 160.

An aspiration tube 10, among the aspiration tube 10a and the aspiration tube 10b, that has aspirated a liquid dispenses the aspirated liquid into a reaction container 93. The aspiration tube 10a dispenses an aspirated sample into the reaction container 93. The aspiration tube 10b dispenses an aspirated reagent into the reaction container 93.

The movement mechanism 40 moves the aspiration tubes 10 to positions directly above reagent supply units 161a and 161b (=reagent aspirating position Ph and Pi), the spot application unit 170, the cleaning mechanism 50 (=cleaning position Pj), and the sample supply unit 126, which are aspirating positions, a discharging position, and a cleaning position for the aspiration tube 10a and the aspiration tube 10b. These components are arranged linearly in the X direction in plan view in order from the reagent supply units 161a and 161b through the spot application unit 170 and the cleaning mechanism 50 to the sample supply unit 126.

The aspiration tube 10a and the aspiration tube 10b are connected to a metering syringe 15a for dispending a sample (see FIG. 14) and a metering syringe 15b for dispensing a reagent (see FIG. 14) and aspirate and discharge predetermined amounts of a sample and a reagent, respectively.

(Cleaning Mechanism)

Figure 10:
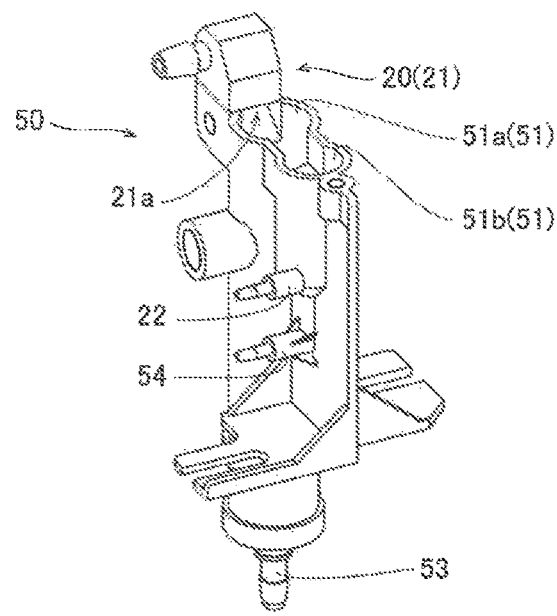
FIG. 10 is a diagram of a perspective view illustrating a cleaning mechanism.

As illustrated in FIG. 10, the cleaning mechanism 50 includes the cleaning liquid discharger 20. The cleaning mechanism 50 includes a cleaning vessel 51 opened at the top so as to receive the cleaning liquid 70 discharged from the cleaning liquid discharger 20.

Figure 11:
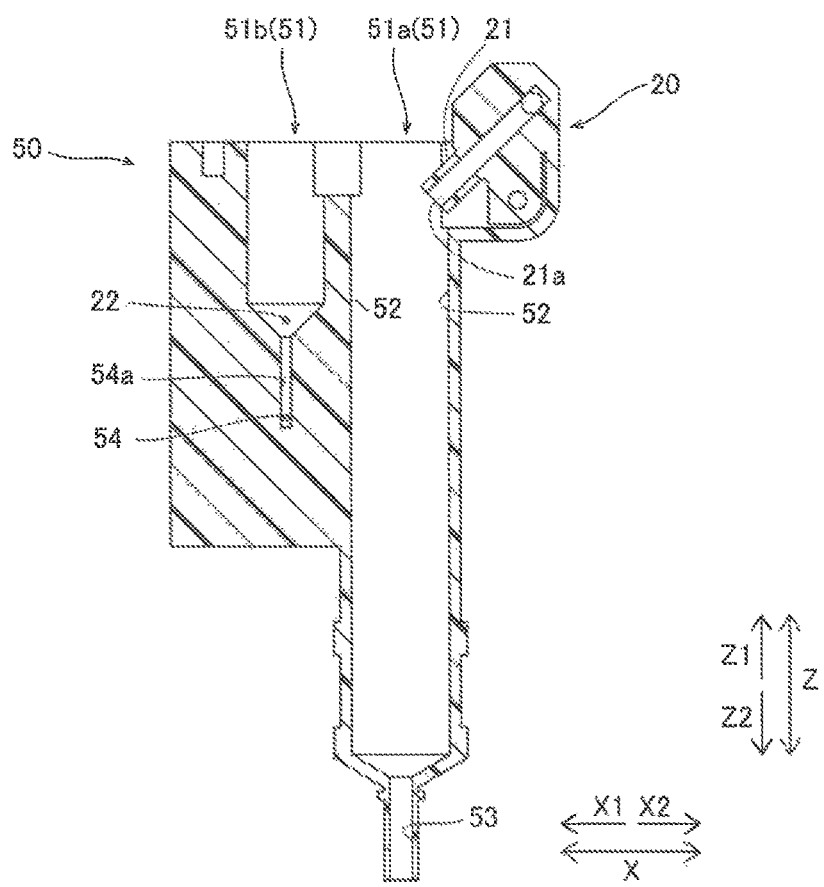
FIG. 11 is a diagram of a longitudinal cross-sectional view illustrating a cleaning mechanism illustrated in FIG. 10.

The cleaning mechanism 50 illustrated in FIGS. 10 and 11 is configured to clean each aspiration tube 10 by using multiple types of cleaning liquids. The cleaning liquid discharger 20 includes: a first discharger 21 that discharges the cleaning liquid 70 or a first cleaning liquid (see FIG. 12); and a second discharger 22 that discharges a second cleaning liquid 72 (see FIG. 13) higher in detergency than the cleaning liquid 70. The cleaning vessel 51 includes a first vessel 51a that receives the cleaning liquid 70 and a second vessel 51b that receives the second cleaning liquid 72. The first vessel 51a and the second vessel 51b both have a tubular shape extending vertically toward the opening at the top, and the aspiration tube 10 can be inserted into them from above. As described later, a droplet DL attached to the tip 11 of the aspiration tube 10 in an embodiment is removed by the cleaning liquid 70 discharged from the first discharger 21.

As illustrated in FIG. 11, the first discharger 21 is provided at the top of the first vessel 51a. The first discharger 21 has a discharge port 21a facing obliquely downward and discharges the cleaning liquid 70 toward an inner wall surface 52 of an upper portion of the first vessel 51a. The discharge port 21a of the first discharger 21 is opened so as to face a portion of the inner wall surface 52 of the first vessel 51a located on the opposite side of the center of the first vessel 51a from a position on the inner wall surface 52. The first discharger 21 discharges the cleaning liquid 70 from one side of the inner wall surface 52 of the first vessel 51a toward a portion of the inner wall surface 52 on the other side across the center of the first vessel 51a. In cleaning of the aspiration tube 10 (see FIG. 12), the aspiration tube 10 is moved so as to contact a flow of the cleaning liquid 70 discharged from the first discharger 21 and traveling through the air before contacting the inner wall surface 52 of the first vessel 51a.

The discharge port 21a of the first discharger 21 has a larger inner diameter than the outer diameter of the aspiration tube 10. Thus, the cleaning liquid 70 discharged from the first discharger 21 forms a flow of a liquid column shape having a larger outer diameter than the outer diameter of the aspiration tube 10 (see FIG. 12).

As illustrated in FIG. 12, the controller 60 causes the cleaning liquid discharger 20 to discharge the cleaning liquid 70 obliquely downward so as to form a substantially straight columnar flow of the cleaning liquid 70. Specifically, the cleaning liquid 70 is discharged from the first discharger 21 at such a pressure that the flow of the cleaning liquid 70 collides with the inner wall surface 52 while maintaining the form of a straight flow before curving in a parabola with the effect of gravity. Since the cleaning liquid 70 is discharged obliquely downward, the variation in the position of the surface 71 of the cleaning liquid 70 due to subtle changes in hydraulic pressure or the like is reduced as compared to a case where the cleaning liquid 70 is discharged upward, for example. Moreover, since the discharge pressure obtained is so high that the flow of the cleaning liquid 70 forms a substantially straight columnar shape, the subtle changes in hydraulic pressure or the like have a low impact. This also reduces the variation in the position of the surface 71 of the cleaning liquid 70.

As illustrated in FIG. 11, the first vessel 51a has a drainage port 53 for the cleaning liquid 70 at the bottom. While the cleaning liquid 70 is discharged from the first discharger 21, the cleaning mechanism 50 continuously drains the cleaning liquid 70 received in the first vessel 51a from the drainage port 53. The flow rate of the drainage through the drainage port 53 is larger than or equal to the flow rate of the discharge by the first discharger 21. Thus, during the cleaning of the aspiration tube 10, the cleaning liquid 70 does not accumulate in the first vessel 51a, so that the aspiration tube 10 is cleaned at a position above the cleaning liquid 70 flowing inside the first vessel 51a toward the drainage port 53.

Figure 13:
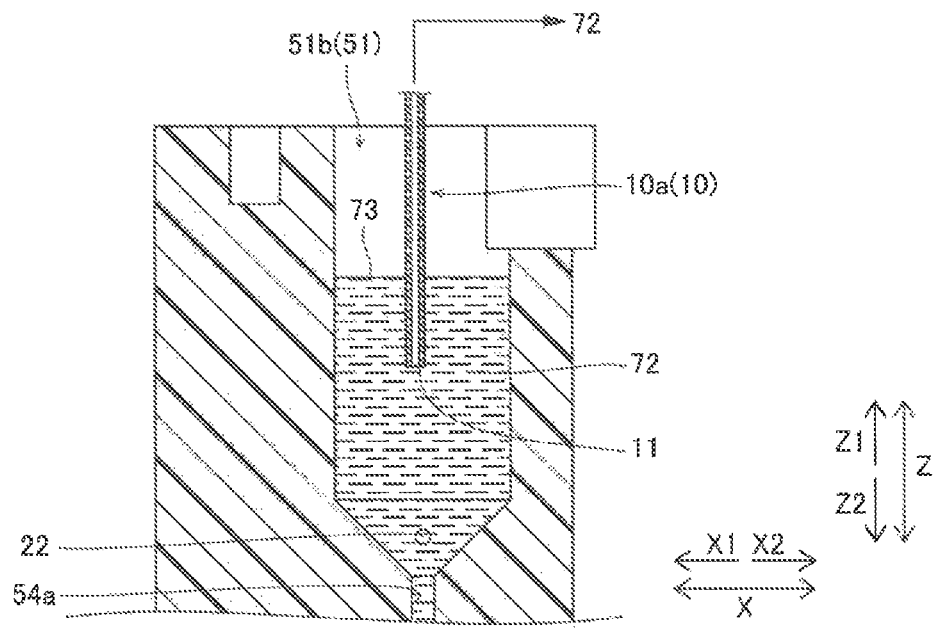
FIG. 13 is a diagram of an enlarged cross-sectional view illustrating cleaning inside a second vessel in a cleaning mechanism.

The second discharger 22 is opened near the bottom of the second vessel 51b, and supplies the second cleaning liquid 72 to the bottom of the second vessel 51b. The second vessel 51b communicates with a drainage port 54 for the second cleaning liquid 72 through a drainage path 54a connected to the bottom. The cleaning mechanism 50 accumulates the second cleaning liquid 72 discharged from the second discharger 22 in the second vessel 51b. When a single cleaning operation on the aspiration tube 10 is finished, the accumulated second cleaning liquid 72 is drained from the drainage port 54. As illustrated in FIG. 13, in cleaning of the aspiration tube 10, the aspiration tube 10 is moved such that the aspiration tube 10 is inserted into the second cleaning liquid 72 accumulated in the second vessel 51b to a position below its liquid surface 73 and thus a cleaning area including the tip 11 is immersed in the second cleaning liquid 72. As a result, immersion cleaning of the aspiration tube 10 is performed with the second cleaning liquid 72.

After the cleaning of the aspiration tube 10 with the second cleaning liquid 72, the controller 60 cleans the aspiration tube 10 with the cleaning liquid 70. When the cleaning with the cleaning liquid 70 is finished, the controller 60 controls the movement mechanism 40 so as to move the tip 11 to a position at which it contacts the surface 71 of the flow of the cleaning liquid 70. As described above, in the method of cleaning the aspiration tube 10 in an embodiment, the aspiration tube 10 is cleaned with the cleaning liquid 70 after the cleaning of the aspiration tube 10 with the second cleaning liquid 72, and a step of decelerating or stopping upward movement of the aspiration tube 10 is performed when the cleaning with the cleaning liquid 70 is finished. Thus, the cleaning of the second cleaning liquid 72 with higher detergency is followed by the cleaning with the cleaning liquid 70 and the removal of the droplet DL. Hence, in the case of performing the cleaning with the second cleaning liquid 72 with higher detergency, not only contamination by the droplet DL is prevented but also contamination by the cleaning component contained in the second cleaning liquid 72 is prevented.

(Cleaning Liquids)

As described above, the aspiration tube 10a is configured to dispense a blood sample. Further, the second cleaning liquid 72 contains a protein-decomposing component while the cleaning liquid 70 contains practically no protein-decomposing component or contains the protein-decomposing component at a lower concentration than the second cleaning liquid 72.

In one example, the second cleaning liquid 72 is an aqueous hypochlorite solution. The proteolytic component is hypochlorous acid ion. Oxidative decomposition effects of hypochlorous acid ion and hypochlorous acid derived from hypochlorous acid ion effectively decompose the proteins contained in a sample attached to the aspiration tube 10, thereby preventing contamination. The second cleaning liquid 72 is an aqueous hypochlorous acid solution, for example.

Water is an example of the cleaning liquid 70. Besides water, the cleaning liquid 70 can contain an antiseptic or the like, for example. In this case, the concentration of hypochlorite contained in the cleaning liquid 70 as its protein-decomposing component is sufficiently lower than that of the second cleaning liquid 72. By performing the cleaning with the cleaning liquid 70 and the removal of the droplet DL after the cleaning with the second cleaning liquid 72, the protein-decomposing component contained in the second cleaning liquid 72 is prevented from remaining on the cleaned aspiration tube 10.

As a result, the proteins contained in the blood sample are removed by the second cleaning liquid 72, so that contamination in the next sample aspiration by the aspiration tube 10 is effectively prevented. Further, it is effectively prevented that in the next sample aspiration the proteins contained in the blood sample are decomposed due to contamination by the second cleaning liquid 72 and thereby affect the measurement accuracy.

(Fluid Circuit)

Figure 14:
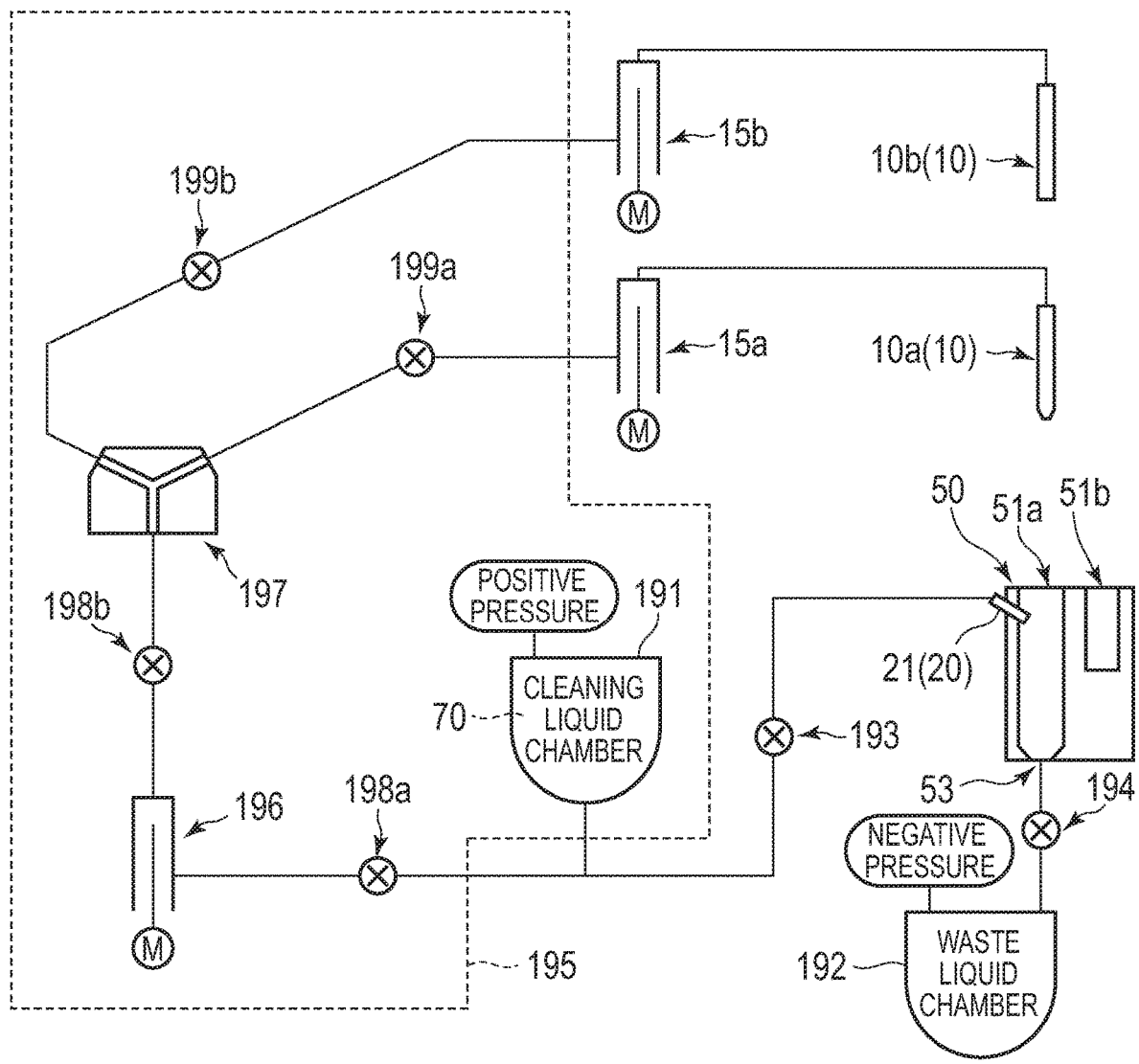
FIG. 14 is a schematic diagram illustrating a fluid circuit that supplies a cleaning liquid to a cleaning mechanism and aspiration tubes.

The fluid circuit that supplies the cleaning liquid 70 to the cleaning mechanism 50 is described with reference to FIG. 14. Note that only a supply path for the cleaning liquid 70 is illustrated in FIG. 14, and description of a supply path for the second cleaning liquid 72 to the second discharger 22 is omitted.

The specimen measuring apparatus 100 includes a cleaning liquid chamber 191, a waste liquid chamber 192, a valve 193, and a valve 194.

The first discharger 21 of the cleaning mechanism 50 is connected to the cleaning liquid chamber 191, in which the cleaning liquid 70 is stored, through a flow path provided with the valve 193. Also, the cleaning liquid chamber 191 is connected to a positive pressure source. When the valve 193 is opened, positive pressure causes the cleaning liquid 70 to be supplied from the cleaning liquid chamber 191 to the first discharger 21 and discharged into the first vessel 51a. The discharge of the cleaning liquid 70 from the first discharger 21 stops when the valve 193 is closed.

The drainage port 53 of the first vessel 51a is connected to the waste liquid chamber 192 through a flow path provided with the valve 194. The waste liquid chamber 192 is connected to a negative pressure source. When the valve 194 is opened, negative pressure causes the cleaning liquid 70 to be drained from the drainage port 53 of the first vessel 51a into the waste liquid chamber 192. The drainage stops when the valve 194 is closed.

The specimen measuring apparatus 100 includes a cleaning liquid supply unit 195 that supplies the cleaning liquid 70 to each aspiration tube 10. The cleaning liquid supply unit 195 includes a pressure syringe 196, a branching part 197, a valve 198a and a valve 198b, and a valve 199a and a valve 199b.

The pressure syringe 196 is connected to the cleaning liquid chamber 191 through a flow path provided with the valve 198a. When the valve 198a is opened, positive pressure causes the cleaning liquid 70 to be supplied from the cleaning liquid chamber 191 into the pressure syringe 196. The supply of the cleaning liquid 70 stops when the valve 198a is closed.

The pressure syringe 196 is connected to the branching part 197 through a flow path provided with the valve 198b. Opening the valve 198b enables supply of the cleaning liquid 70 to the branching part 197, while closing the valve 198b disables the supply.

The branching part 197 is connected to the metering syringe 15a for dispensing a sample through a flow path provided with the valve 199a and connected to the metering syringe 15b for dispensing a reagent through a flow path provided with the valve 199b. The destination of supply of the liquid from the pressure syringe 196 can be selected between the aspiration tube 10a for dispensing a sample and the aspiration tube 10b for dispensing a reagent by selectively opening one of the valve 199a and the valve 199b and closing the other.

The pressure syringe 196 is capable of pressurizing and supplying the cleaning liquid 70 by storing the cleaning liquid 70 in the syringe and operating a piston with a drive source, such as a motor. Thus, in cleaning of the aspiration tube 10a or 10b, the inner wall surface of the aspiration tube 10 can be effectively cleaned by supplying the cleaning liquid 70 under high pressure with the pressure syringe 196 and discharging it from the tip 11.

The controller 60 controls the supply pressure of the pressure syringe 196 so as to make the flow of the cleaning liquid 70 inside the aspiration tube 10a or 10b turbulent. This enables effective cleaning of the inside of the aspiration tube 10. The Reynolds number of the cleaning liquid 70 flowing through the aspiration tube 10 is 4000 or more, for example.

(Cleaning Operations)

Next, operations in the cleaning of the aspiration tube 10 by the cleaning mechanism 50 are described. In this section, the cleaning of the aspiration tube 10a is described. The same cleaning operations may be employed for the cleaning of the aspiration tube 10a and the cleaning of the aspiration tube 10b. Different cleaning operations may be employed for the cleaning of the aspiration tube 10a and the cleaning of the aspiration tube 10b. The method of cleaning an aspiration tube in an embodiment is performed on at least the aspiration tube 10a for dispensing a blood sample.

The cleaning liquid 70 is continuously discharged from the first discharger 21 in the cleaning in the first vessel 51a, while the second cleaning liquid 72 discharged from the second discharger 22 is stored in the second vessel 51b in the cleaning in the second vessel 51b.

As illustrated in FIG. 15, the controller 60 firstly controls the movement mechanism 40 so as to move the aspiration tube 10a to directly above the first vessel 51a and then perform a first cleaning operation on the aspiration tube 10a with the cleaning liquid 70 inside the first vessel 51a. Then, the controller 60 controls the movement mechanism 40 so as to move the aspiration tube 10a to directly above the second vessel 51b and then perform a second cleaning operation on the aspiration tube 10a with the second cleaning liquid 72 inside the second vessel 51b. Then, the controller 60 controls the movement mechanism 40 so as to move the aspiration tube 10a to directly above the first vessel 51a, then perform cleaning of the aspiration tube 10a with the cleaning liquid 70 inside the first vessel 51a, and perform a third cleaning operation of bringing the tip 11 of the aspiration tube 10a into contact with the surface 71 of the flow of the cleaning liquid 70 when the cleaning is finished. In the following description, the height position of the aspiration tube 10 is based on the position of the tip 11.

In the first cleaning operation, in step S11, the controller 60 moves the aspiration tube 10a downward to insert the aspiration tube 10a into the first vessel 51a such that the aspiration tube 10a directly contacts the flow of the cleaning liquid 70 over a predetermined cleaning target area larger than the area of the aspiration tube 10a which can contact a sample or a reagent in dispensing. Then in step S12, the movement mechanism 40 moves the aspiration tube 10a upward and then moves it from directly above the first vessel 51a to directly above the second vessel 51b.

In the second cleaning operation, in step 513, the controller 60 moves the aspiration tube 10a downward to insert the aspiration tube 10a into the second vessel 51b to such a position that the cleaning target area of the aspiration tube 10a is immersed in the second cleaning liquid 72. In step S14, the controller 60 stops the movement mechanism 40 to perform immersion cleaning for a predetermined time. In doing so, the controller 60 controls the metering syringe 15a so as to cause the aspiration tube 10a to aspirate the second cleaning liquid 72 (see FIG. 13) to thereby fill the inside of the aspiration tube 10a with the second cleaning liquid 72 as well. After the elapse of the predetermined time, in step S15, the controller 60 causes the movement mechanism 40 to move the aspiration tube 10a upward and move the aspiration tube 10a from directly above the second vessel 51b to directly above the first vessel 51a.

In the third cleaning operation, in step 516 after moving the aspiration tube 10a to directly above the first vessel 51a, the controller 60 controls the movement mechanism 40 so as to move the aspiration tube 10a downward into the first vessel 51a such that the aspiration tube 10a contacts the flow of the discharged cleaning liquid 70. As a result, the outer surface of the aspiration tube 10a is cleaned.

In step S17, when moving the aspiration tube 10a downward into the cleaning vessel 51 (first vessel 51a), the controller 60 raises and lowers the aspiration tube 10a while keeping the aspiration tube 10a in contact with the flow of the cleaning liquid 70 discharged from the cleaning liquid discharger 20. Thus, since the aspiration tube 10a is raised and lowered, the portion of the aspiration tube 10a to be cleaned is brought into direct contact with the flow of the cleaning liquid 70 multiple times. This enables effective cleaning as compared to a case where the aspiration tube 10a is simply moved downward.

The controller 60 moves the aspiration tube 10a downward until a portion of the aspiration tube 10a above the tip 11 contacts the flow of the cleaning liquid 70. Thus, the aspiration tube 10 is moved downward into the first vessel 51a from a home position HO above the cleaning liquid 70 at which the aspiration tube 10 does not contact the cleaning liquid 70 to a height position H2 at which the upper end of the cleaning target area contacts the flow of the cleaning liquid 70. The controller 60 moves the aspiration tube 10a downward into the cleaning vessel 51 while continuing the cleaning with the cleaning liquid 70 discharged from the cleaning liquid discharger 20 and the drainage of the cleaning liquid 70 from the cleaning vessel 51. As described above, in the method of cleaning the aspiration tube 10 in an embodiment, the cleaning liquid 70 is discharged onto the outer side surface of the aspiration tube 10 inside the cleaning vessel 51, and the method includes a step of moving the aspiration tube 10 downward inside the cleaning vessel 51 while continuing the discharge of the cleaning liquid 70 onto the outer side surface of the aspiration tube 10 and the drainage of the cleaning liquid 70 from the cleaning vessel 51. Thus, the aspiration tube 10 is not immersed in the cleaning liquid 70 accumulated in the cleaning vessel 51. The aspiration tube 10 is cleaned without contacting the cleaning liquid 70 accumulated in the cleaning vessel 51. This enables the aspiration tube 10 to avoid contacting the cleaning liquid 70 that has once contacted the aspiration tube 10 and taken dirt in and therefore effectively prevents the occurrence of contamination.

When moving the aspiration tube 10a downward into the cleaning vessel 51, the controller 60 performs control that causes the cleaning liquid 70 to be discharged from the tip 11 into the cleaning vessel 51 by supplying the cleaning liquid 70 into the aspiration tube 10a (see the dashed-line portion in the FIG. 12). The cleaning liquid 70 is discharged after the tip 11 is positioned inside the cleaning vessel 51 (first vessel 51a). Thus, in the step of moving the aspiration tube 10 downward inside the cleaning vessel 51, the cleaning liquid 70 is discharged from the tip 11 into the cleaning vessel 51 by supplying the cleaning liquid 70 into the aspiration tube 10. In this manner, the inner surface of the aspiration tube 10 is cleaned by the discharge of the cleaning liquid 70 from the tip 11 in parallel with the cleaning of the outer surface of the aspiration tube 10 with the cleaning liquid 70. Here, if the cleaning liquid 70 is accumulated in the cleaning vessel 51, the cleaning liquid 70 discharged from the tip 11 hits the liquid surface and the cleaning liquid 70 may be splashed and attached to the aspiration tube 10. However, even when the cleaning liquid 70 is discharged from the tip 11 into the cleaning vessel 51, the continuous drainage of the cleaning liquid 70 from the cleaning vessel 51 prevents the re-attachment of the cleaning liquid 70 to the aspiration tube 10.

In step S18, the controller 60 brings the portion of the aspiration tube 10a above the tip 11 into contact with the flow of the cleaning liquid 70 to thereby clean the portion, and moves the aspiration tube 10a upward with the cleaning liquid 70 in contact with the aspiration tube 10a. That is, the aspiration tube 10 is moved upward after the downward movement of the aspiration tube 10. Thus, the aspiration tube 10 is moved upward after the aspiration tube 10 is cleaned inside the cleaning vessel 51. This prevents the droplet DL (see FIG. 1B) from remaining at the tip 11 of the aspiration tube 10 even after the sufficient cleaning is performed.

The controller 60 lowers the movement speed of the aspiration tube 10a when the tip 11 is about to be positioned at a position H1 at which the tip 11 contacts the surface 71 of the flow of the cleaning liquid 70, and stops the aspiration tube 10a at the position H1, at which the tip 11 contacts the surface 71 of the flow of the cleaning liquid 70. In step S19, the controller 60 stops the aspiration tube 10a for a predetermined time. The predetermined time is 0.5 second, for example. As described above, in the step of decelerating or stopping the upward movement of the aspiration tube 10, the tip 11 is moved to the position H1, at which the tip 11 contacts the surface 71 of the flow of the discharged cleaning liquid 70, and the upward movement of the aspiration tube 10 is stopped at the position H1, at which the tip 11 contacts the surface 71 of the flow of the cleaning liquid 70. Thus, the state where only the tip 11 of the aspiration tube 10 contacts the surface 71 of the flow of the cleaning liquid 70 is maintained for a long time by the deceleration or stopping of the upward movement of the aspiration tube 10. This enables more reliable removal of the droplet DL from the tip 11 of the aspiration tube 10. As mentioned above, the upward movement of the aspiration tube 10 may be decelerated.

In step S20, after positioning the tip 11 at the surface 71 of the flow of the cleaning liquid 70, the controller 60 moves the aspiration tube 10a further upward to thereby move the aspiration tube 10a to a position at which it does not contact the cleaning liquid 70. As a result, the tip 11 is moved away from the cleaning liquid 70 with the droplet DL removed from the tip 11. This prevents re-attachment of the cleaning liquid 70 to the tip 11. Thus, the aspiration tube 10 is moved upward from the position H1 to the home position HO above it, at which the aspiration tube 10 does not contact the cleaning liquid 70.

(Specific Example of Third Cleaning Operation)

FIG. 16 is a timing chart illustrating switching of operation (on/off) of each component involved in a cleaning operation on the aspiration tube 10. The direction toward the bottom of FIG. 16 is the direction of the passage of time. A specific example of the third cleaning operation is presented with reference to FIGS. 16, 15, and 14. The third cleaning operation starts in the state where the aspiration tube 10a is positioned directly above the first vessel 51a after the second cleaning operation is finished. In this state, the height position HO of the aspiration tube 10a corresponds to the home position of the motor 45 (45a).

The aspiration tube 10a is moved downward from a timing t0 to a timing t1. The valve 194 and the valve 193 are opened and the valve 198a is closed at the timing t1 while the downward movement is still being made. As a result, the cleaning liquid 70 is discharged from the first discharger 21 and the cleaning liquid 70 is drained from the drainage port 53 of the first vessel 51a. The aspiration tube 10a is moved downward to the position H2, at which its portion above the tip 11 contacts the flow of the cleaning liquid 70.

At a timing t2, the valve 199a and 198b are opened, so that the aspiration tube 10a and the pressure syringe 196 communicate with each other. Also, the pressure syringe 196 and the metering syringe 15a are driven, so that the cleaning liquid 70 under high pressure is supplied into the aspiration tube 10a and the cleaning liquid 70 is discharged from the opening at the tip 11 into the first vessel 51a.

The pressure syringe 196 stops being driven at a timing t3, and the metering syringe 15a stops being driven at a timing t4. This ends the discharge of the cleaning liquid 70 from the aspiration tube 10a.

The aspiration tube 10a is moved upward from a timing t5 to a timing t6, and the aspiration tube 10a is moved downward from a timing t7 to a timing t8. Thus, the aspiration tube 10a is raised and lowered to thereby repetitively clean the cleaning target area via contact with the flow of the cleaning liquid 70. Note that the valve 198a is opened at the timing t5 to thereby supply the cleaning liquid 70 to the pressure syringe 196 for the next cleaning.

The aspiration tube 10a is moved upward from the position H2 from a timing t9 to a timing t10. The aspiration tube 10a is moved to the position H1, at which the tip 11 contacts the surface 71 of the flow of the cleaning liquid 70. Note that position information 63 (see FIG. 17) on the aspiration tube 10a at the timing at which the tip 11 contacts the surface 71 of the flow of the cleaning liquid 70 has been obtained in advance before the cleaning of the aspiration tube 10a. The controller 60 controls the movement mechanism 40 based on the position information 63 so as to move the aspiration tube 10a to the position H1, at which the tip 11 contacts the surface 71 of the flow of the cleaning liquid 70.

The aspiration tube 10a is stopped from the timing t10 to a timing t11 at the position H1, at which the tip 11 contacts the surface 71 of the flow of the cleaning liquid Then, the aspiration tube 10a is moved upward from the timing t11 to a timing t15 such that the aspiration tube 10a is moved to the home position H0, at which it does not contact the cleaning liquid 70.

Note that in the period from the timing t11 to the timing t15, the valve 198b and the valve 199a are closed at the timing t12, the valve 193 is closed at the timing t13, and the valve 194 is closed at the timing t14.

(Obtaining of Position Information on Position at which Tip Makes Contact)

As illustrated in FIG. 17, an embodiment further involves a step of obtaining the position information 63 on the position of the aspiration tube 10 at which the tip 11 of the aspiration tube 10 contacts the surface 71 of the flow of the cleaning liquid 70, before the discharge of the cleaning liquid 70 onto the outer side surface of the aspiration tube 10. Based on the position information 63, the aspiration tube 10 is stopped in a state where the tip 11 of the aspiration tube 10 contacts the surface 71 of the flow of the cleaning liquid 70. Thus, unlike a case where, for example, the liquid surface is detected during the cleaning of the aspiration tube 10 to detect the position H1, at which the tip 11 contacts the surface 71 of the flow of the cleaning liquid 70, the tip 11 is brought into contact with the surface 71 of the flow of the cleaning liquid 70 only by moving and stopping the aspiration tube 10 to and at a position obtained in advance. This eliminates the need to, for example, move the aspiration tube 10 at low speed for detection of the liquid surface, and thus enables the tip 11 to be brought into contact with the surface 71 of the flow of the cleaning liquid 70 in as short a time as possible. Accordingly, a longer time can be allotted for the cleaning of the aspiration tube 10.

Specifically, the specimen measuring apparatus 100 includes the liquid surface detector 65, which detects contact of the tip 11 with the surface 71 of the flow of the cleaning liquid 70. Before the discharge of the cleaning liquid 70 onto the outer side surface of the aspiration tube 10 from the cleaning liquid discharger 20, the controller 60 obtains the position information 63 on the aspiration tube 10 at the timing at which the tip 11 of the aspiration tube 10 contacts the surface 71 of the flow of the cleaning liquid 70, based on the result of the detection by the liquid surface detector 65, and performs control that moves the aspiration tube 10 while causing the cleaning liquid discharger 20 to discharge the cleaning liquid 70 onto the outer side surface of the aspiration tube 10, and stop the aspiration tube 10 based on the position information 63 in the state where the tip 11 of the aspiration tube 10 contacts the surface 71 of the flow of the cleaning liquid 70. The controller 60 stores the obtained position information 63 in a memory 61. In the cleaning of the aspiration tube 10, the controller 60 reads the position information 63 out of the memory 61 and controls the position of the aspiration tube 10 based on the position information 63.

In an example, the liquid surface detector 65 includes a capacitive liquid surface detection sensor that detects the liquid surface based on a change in the capacitance of the aspiration tube 10. Specifically, the capacitance changes from a state where the aspiration tube 10 is out of contact with the cleaning liquid 70 to a state where the aspiration tube 10 is in contact with the cleaning liquid 70 and vice versa, based on which contact of the aspiration tube 10 with the surface 71 of the flow of the cleaning liquid 70 is detected. The liquid surface detector 65 outputs the result of the detection to the controller 60.

The controller 60 detects contact of the tip 11 with the surface 71 of the flow of the cleaning liquid 70 with the liquid surface detector 65, and obtains the position information 63 based on the result of the detection by the liquid surface detector 65. Thus, obtained is the position at which the tip 11 actually contacted the surface 71 of the flow of the cleaning liquid 70, and therefore the position information 63 is accurately obtained.

The position information 63 is information for moving the aspiration tube 10 with the movement mechanism 40 to the position H1, at which the tip 11 contacts the surface 71 of the flow of the cleaning liquid 70. Specifically, the position information 63 is obtained as the number of pulses from the home position H0 of the motor 45 (45a, 45b) that vertically moves the aspiration tube 10. The controller 60 brings the tip 11 into contact with the surface 71 of the flow of the cleaning liquid 70 by moving the aspiration tube 10 to a position coordinate specified by the number of pulses being the position information 63.

In an embodiment, the operation of moving the aspiration tube 10 for obtaining the position information 63 (see FIG. 17) and the operation of moving the aspiration tube 10 for bringing the tip 11 into contact with the surface 71 of the flow of the cleaning liquid 70 in the cleaning of the aspiration tube 10 (see FIG. 19) are different.

Specifically, in the step of obtaining the position information 63, the aspiration tube 10 is moved downward from above the flow of the discharged cleaning liquid 70 to bring the tip 11 into contact with the cleaning liquid 70. In the cleaning of the aspiration tube 10, the aspiration tube 10 is moved upward based on the position information 63 from the position at which the portion above the tip 11 contacts the flow of the cleaning liquid 70 to the position at which the tip 11 contacts the surface 71 of the flow of the cleaning liquid 70.

Here, as illustrated in FIG. 17, consider an operation MV1 of moving the aspiration tube 10 downward from the home position H0 through the position H1 to the position H2, and an operation MV2 of moving the aspiration tube 10 upward from the position H2 through the position H1 to the home position H0. Note that for the sake of illustration, the operations MV1 and MV2 are illustrated at horizontally different positions, but the positions at which the operations take place are the same position.

In the case of detecting contact between the tip 11 and the surface 71 of the cleaning liquid 70 with the capacitive liquid surface detector 65, detected is the change in its detection signal either at a moment when the aspiration tube 10 and the cleaning liquid 70 transition from a non-contacting state to a contacting state in the operation MV1 (a moment of reaching the position H1 from the position H0) or at a moment when the aspiration tube 10 and the cleaning liquid 70 transition from the contacting state to the non-contacting state in the operation MV2 (a moment of passing the position H1 from the position H2 side).

Figure 18:
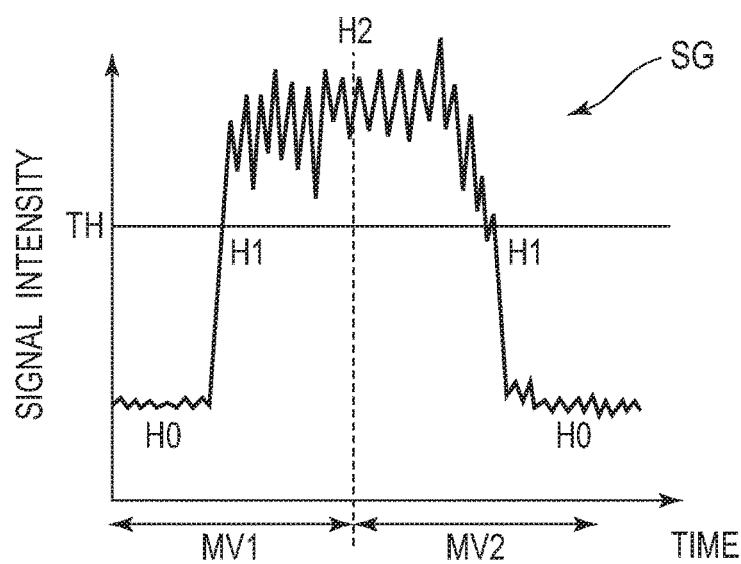
FIG. 18 is a diagram of a graph illustrating changes in an output signal of a liquid surface detector with movement of an aspiration tube.

At these moments, the output signal of the liquid surface detector 65 changes as in a graph SG illustrated in FIG. 18. At the position H0, at which the aspiration tube 10 and the cleaning liquid 70 are out of contact with each other, the intensity of the signal of the liquid surface detector 65 is stable at a low level. When the aspiration tube 10 is moved from the position H0 to the position H1 by the operation MV1, the signal intensity exceeds a threshold value TH, so that the tip 11 is detected to come into contact with the surface 71 of the flow of the cleaning liquid 70. Since the cleaning liquid 70 is not stationary but is forming a flow, the detection signal is not stable while the cleaning liquid 70 and the aspiration tube 10 are in the contacting state, and the signal intensity changes across wide ranges from the position H1 to the position H2. Then, as the aspiration tube 10 is moved from the position H2 to the position H0 by the operation MV2, the signal intensity falls below the threshold value TH when the aspiration tube 10 and the cleaning liquid 70 come out of contact with each other around the position H1. As can be seen from the graph SG, the change is accurately detected during the downward movement to the position H1 from the position H0, at which the signal intensity is stable at a low level. During the upward movement to the position H1 from the position H2, on the other hand, the signal intensity changes across wide ranges and is unstable and therefore the accuracy of detection of the timing at which the signal intensity falls below the threshold value TH is lower than the detection accuracy during the downward movement by the operation MV1. For this reason, when the position information 63 is obtained, it is possible to accurately obtain the contact position H1 with the operation MV1, in which the aspiration tube 10 is moved downward from above the flow of the discharged cleaning liquid 70 to thereby bring the tip 11 into contact with the cleaning liquid 70. As illustrated in FIG. 17, the controller 60 obtains, as the position information 63, a number of pulses N1 from when the tip 11 is at the home position H0 to when the tip 11 reaches the position H1 therefrom and the signal intensity exceeds the threshold value TH.

On the other hand, as illustrated in FIG. 19, in the cleaning of the aspiration tube 10, the aspiration tube 10 is moved upward based on the position information 63 from the position H2, at which the portion above the tip 11 contacts the flow of the cleaning liquid 70, to the position H1, at which the tip 11 contacts the surface 71 of the flow of the cleaning liquid 70. The aspiration tube 10 may be moved upward based on the position information 63 to the position at which the droplet DL attached to the tip 11 contacts the surface 71 of the flow of the cleaning liquid 70. The controller 60 positions the tip 11 at the position H1 by moving the aspiration tube 10 upward from the position H2 by a difference obtained by subtracting the number of pulses N1 as the position information 63 from a number of pulses N2 from the home position H0 to the position H2 of the aspiration tube 10 (N2−N1).

Doing this technically entails an error factor such as the backlash of the gears used in the motor 45 or the like. Specifically, when the aspiration tube 10 is moved upward toward the position H1 from the state where it has been moved downward to the position H2, the position of contact between the gears changes, thereby causing a slight error (backlash). Due to the backlash, the upward movement may result in displacement of the position H1 to a slightly lower position than the position H1 detected in the downward movement. In the case where the displacement toward the lower side occurs, the tip 11 is displaced in a direction toward the flow of the cleaning liquid 70, as can be seen from FIG. 19. For this reason, even with the error factor taken into consideration, the tip 11 is reliably brought into contact with the surface 71 of the flow of the cleaning liquid 70.

FIGS. 17 to 19 mentioned above illustrate an example in which the position information 63 on the position of the aspiration tube 10 at which the tip 11 of the aspiration tube 10 contacts the surface 71 of the flow of the cleaning liquid 70 is obtained. Alternatively, position information 63 on the position of the aspiration tube 10 at which the droplet DL attached to the tip 11 of the aspiration tube 10 contacts the surface 71 of the flow of the cleaning liquid 70 (see FIG. 1 F) may be obtained. In this case, in the cleaning of the aspiration tube 10, the aspiration tube 10 is stopped based on the position information 63 in the state where the droplet DL attached to the tip 11 contacts the surface 71 of the flow of the cleaning liquid 70.

The position illustrated in FIG. 1 F, at which the droplet DL attached to the tip 11 of the aspiration tube 10 contacts the surface 71 of the flow of the cleaning liquid 70, is obtained based on the result of detection by the liquid surface detector 65. In an example, in the obtaining of the position information 63, firstly, the cleaning liquid 70 is discharged onto the outer side surface of the aspiration tube 10 to form the droplet DL at the tip 11. Then, contact of the droplet DL with the surface 71 of the flow of the cleaning liquid 70 is detected based on the change in capacitance upon contact of the droplet DL with the surface 71 of the flow of the cleaning liquid 70 from a state of being separated from the surface 71 of the flow of the cleaning liquid 70. The controller 60 obtains position information 63 on the position at which the droplet DL was detected to come into contact with the surface 71 of the flow of the cleaning liquid 70. Alternatively, a position shifted upward by several pulses from the contact position H1, at which the tip 11 of the aspiration tube 10 contacts the surface 71 of the flow of the cleaning liquid 70, may be obtained as the position at which the droplet DL contacts the surface 71 of the flow of the cleaning liquid 70. The number of pulses by which to shift the contact position upward from the contact position H1 can be obtained empirically.

Note that, instead of using a capacitive liquid surface detection sensor, image recognition may be performed on an image of the tip 11 captured by a camera to obtain the position information 63. The image recognition with a camera is also suitable for detection of the position at which the droplet DL contacts the surface 71 of the flow of the cleaning liquid 70. Alternatively, a distance measurement apparatus, such as a laser rangefinder, may be used to obtain the position information 63. Alternatively, the aspiration tube 10 may be caused to approach the flow of the cleaning liquid 70 while performing an aspiration operation by being supplied with negative pressure, and contact of the tip 11 with the surface 71 of the flow of the cleaning liquid 70 may be detected based on the change in the aspiration pressure upon contact of the tip 11 with the surface 71. Alternatively, the aspiration tube 10 may be caused to approach the flow of the cleaning liquid 70 with a sonic or ultrasonic vibration applied thereto, and contact of the tip 11 with the surface 71 of the flow of the cleaning liquid 70 may be detected based on the change in the vibration frequency or amplitude upon contact of the tip 11 with the surface 71.

The timing of obtaining the position information 63 is not particularly limited as long as it is before the cleaning of the aspiration tube 10. For example, the position information 63 may be obtained at timings such as when the specimen measuring apparatus 100 is powered on, when the specimen measuring apparatus 100 performs a preparation operation before transitioning from a standby state to a measurement state for performing a measurement operation, when the specimen measuring apparatus 100 is waiting for a next measurement order due to absence of input of a measurement order of a sample, when measurement operations have been performed on a predetermined number of samples since the obtaining of the last position information 63, and so on.

Figure 20:
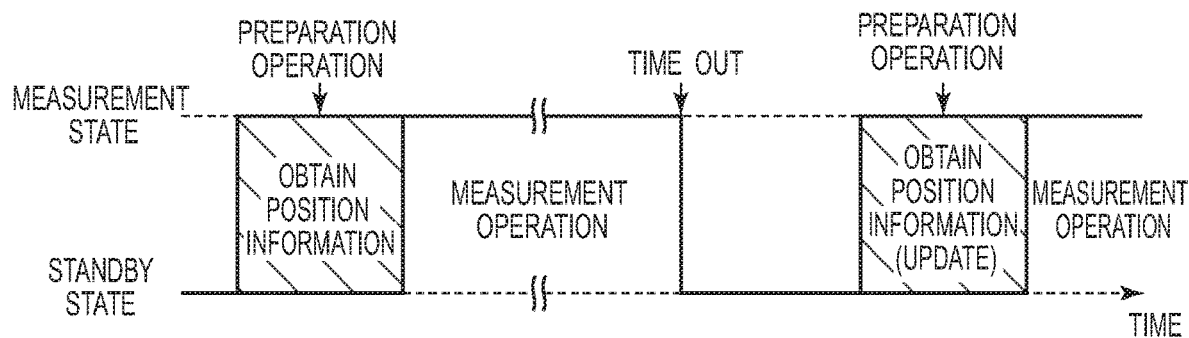
FIG. 20 is a diagram of a timing chart illustrating an example of timings for obtaining position information.

In one example, as illustrated in FIG. 20, the controller 60 obtains the position information 63 when the specimen measuring apparatus 100 performs a preparation operation before transitioning from the standby state to the measurement state for performing a measurement operation. The preparation operation includes operation checks on mechanisms, detection of the home position of the movement mechanism 40, and so on. The preparation operation is carried out firstly when the first measurement operation is to be performed from the standby state after a power-on. A measurement operation is performed upon input of a measurement order for a sample into the specimen measuring apparatus 100. The specimen measuring apparatus 100 times out and transitions to the standby state if, for example, no next measurement order is inputted for a predetermined continuous time after a measurement operation is performed based on a measurement order. Then, upon input of a measurement order for a sample, the specimen measuring apparatus 100 performs the preparation operation and starts a measurement operation.

At each of these timings for carrying out the preparation operation, the controller 60 obtains position information 63 and updates the position information 63. This reduces a position variation due to an uncontrollable factor during operation of the specimen measuring apparatus 100, and reduces displacement of the position at which the tip 11 contacts the surface 71 of the flow of the cleaning liquid 70.

(Control Configuration of Specimen Measurement System)

Next, a control configuration of the specimen measuring apparatus 100 is described with reference to FIG. 21. Note that a control configuration of the blood coagulation measuring apparatus 200 is not described.

Figure 21:
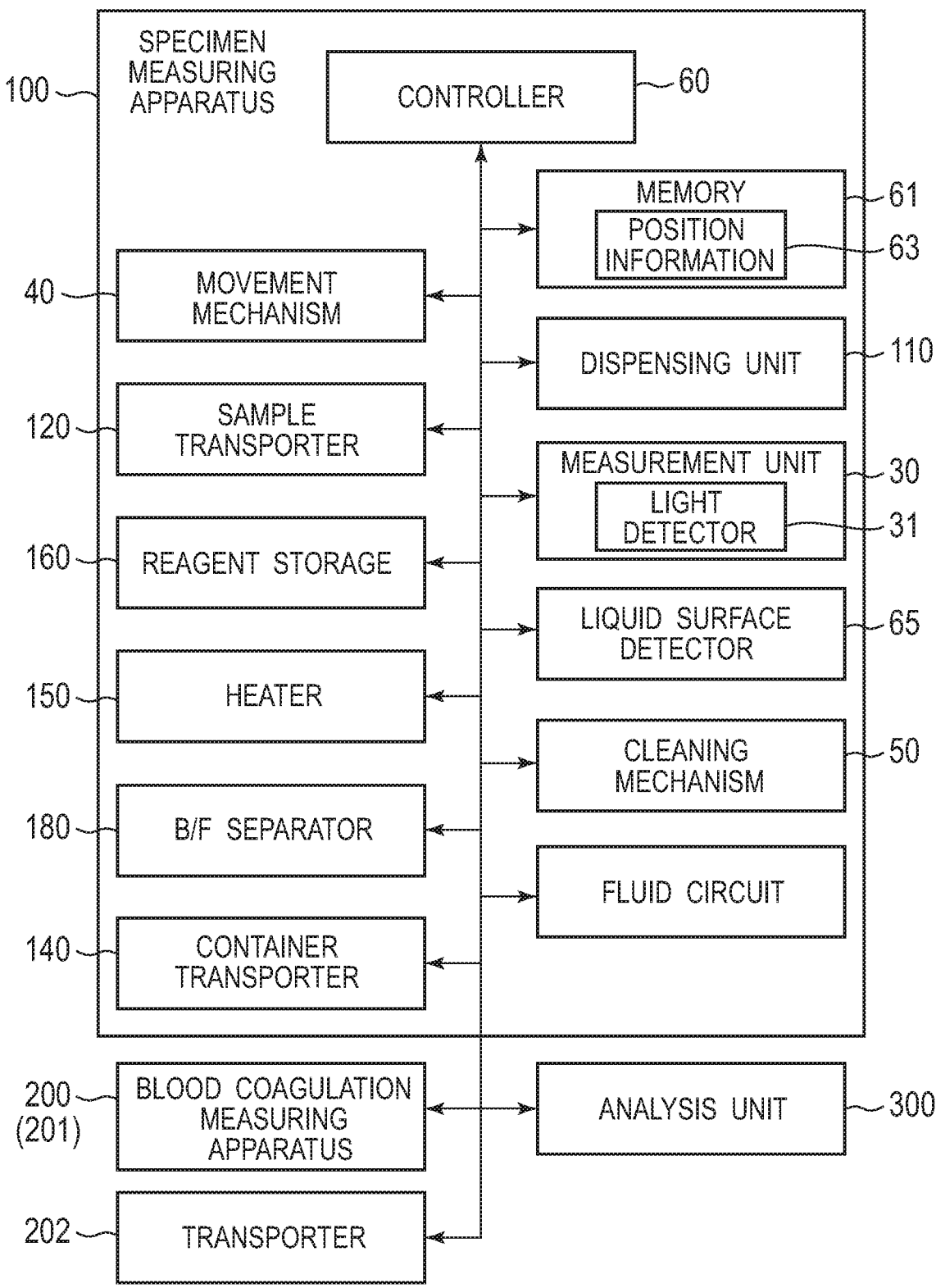
FIG. 21 is a block diagram illustrating an example control configuration of a specimen measuring apparatus.

As illustrated in FIG. 21, the specimen measuring apparatus 100 includes the controller 60 and the memory 61.

The controller 60 includes a processor, such as a CPU or an FPGA. The memory 61 includes a volatile and/or non-volatile storage, such as a ROM, a RAM, or a hard disk drive. The processor functions as a controller of the specimen measuring apparatus 100 by executing a control program stored in the memory. The controller 60 controls the operations of the above-described components of the specimen measuring apparatus 100.

The specimen measuring apparatus 100 includes an analysis unit 300. In an example, the analysis unit 300 is configured as a personal computer. The analysis unit 300 includes a processor, such as a CPU, and storages, such as a ROM, a RAM, and a hard disk drive, for example. The processor functions as the analysis unit 300 of the specimen measuring apparatus 100 by executing a control program stored in the memory.

The analysis unit 300 is electrically connected to the specimen measuring apparatus 100 and the blood coagulation measuring apparatus 200. Also, the analysis unit 300 analyzes the results of measurement by the specimen measuring apparatus 100 and the blood coagulation measuring apparatus 200. The analysis unit 300 is also connected to a host computer through a network, and obtains measurement orders for the apparatuses from the host computer. The analysis unit 300 controls the specimen measuring apparatus 100 and the blood coagulation measuring apparatus 200 such that they sequentially execute received measurement orders.

(Overview of Immunoassay)

In the configuration example illustrated in FIGS. 6 to 21, an immunoassay is performed using the R1 reagent to the R5 reagent, as described above. An instance where a test substance 81 is hepatitis B surface antigen (HBsAg) is described as an example of the immunoassay with reference to FIG. 22.

Firstly, a sample containing the test substance 81 and the R1 reagent are dispensed into a reaction container 93. The sample is dispensed into the reaction container 93 by the aspiration tube 10a. The R1 reagent is dispensed into the reaction container 93 by the aspiration tube 10b. The R1 reagent contains a capture substance 84 and reacts with and binds to the test substance 81. The capture substance 84 contains a binding substance for the capture substance 84 to bind to a solid-state carrier 82 contained in the R2 reagent.

For this binding between the binding substance and the solid-state carrier, it is possible to utilize a combination of, for example, biotin and avidins, a hapten and an antihapten antibody, nickel and a histidine-tag, glutathione and glutathione S-transferase, or the like. Note that "avidins" mean to include avidin and streptavidin.

In an example, the capture substance 84 is an antibody modified by biotin (biotin antibody). That is, in the capture substance 84, biotin is modified as a binding substance. After the dispensing of the sample and the R1 reagent, the specimen in the reaction container 93 is heated in the heater 150 to a predetermined temperature, so that the capture substance 84 and the test substance 81 bind to each other.

Then, the R2 reagent is dispensed into the reaction container 93 by the aspiration tube 10b. The R2 reagent contains the solid-state carrier 82. The solid-state carrier 82 binds to the binding substance in the capture substance 84. In an example, the solid-state carrier 82 is a magnetic particle to which is fixed streptavidin, which binds to biotin (StAvi-bound magnetic particle). The streptavidin of the StAvi-bound magnetic particle reacts with and binds to biotin, which is a binding substance. After the dispensing of the R2 reagent, the specimen in the reaction container 93 is heated in the heater 150 to a predetermined temperature. As a result, the test substance 81 and the capture substance 84 bind to the solid-state carrier 82.

The test substance 81 and the capture substance 84 formed on the solid-state carrier 82 and the unreacted capture substance 84 are separated from each other in a primary B/F separation process by the B/F separator 180. The reaction container 93 is set in a processing port of the B/F separator 180. The B/F separator 180 then executes each of steps of aspirating a liquid-phase substance and discharging a cleaning liquid with the cleaning unit 182 under a magnetically attracting condition provided by the magnetic source 181 and performing stirring or shaking under a non-magnetically attracting condition once or multiple times. By the primary B/F separation process, unnecessary components such as the unreacted capture substance 84 are removed from inside the reaction container 93. At the end of the primary B/F separation process, the immunoassay proceeds to the next step in a state where the liquid-phase substance in the reaction container 93 has been aspirated.

Figure 22:
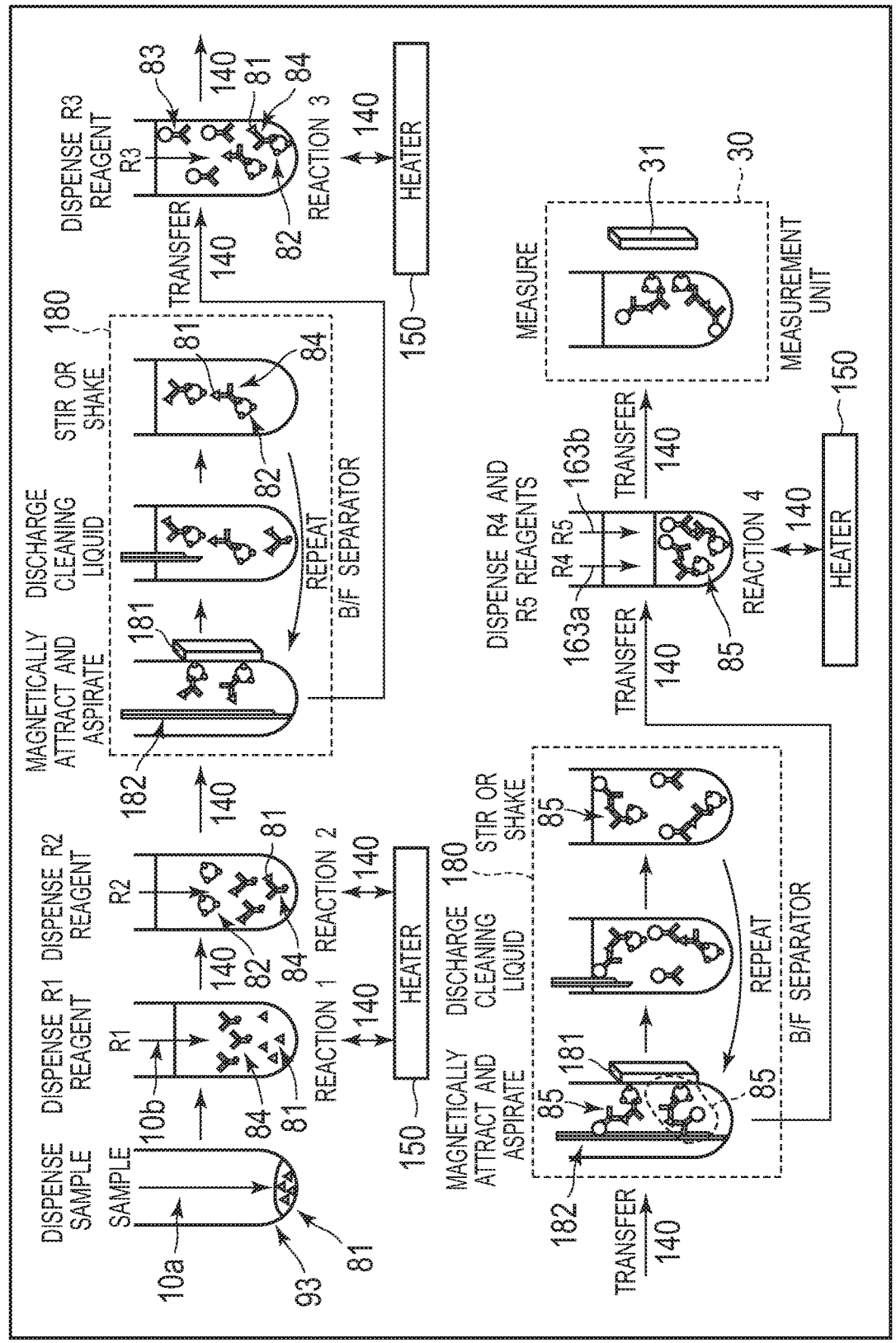
FIG. 22 is a diagram illustrating a measurement process by a specimen measuring apparatus.

Then, the R3 reagent is dispensed into the reaction container 93 by the aspiration tube 10b. The R3 reagent contains a labeled substance 83 and reacts with and binds to the test substance 81. After the dispensing of the R3 reagent, the specimen in the reaction container 93 is heated in the heater 150 to a predetermined temperature. As a result, an immune complex 85 containing the test substance 81, the labeled substance 83, and the capture substance 84 is formed on the solid-state carrier 82. In the example of FIG. 22, the labeled substance 83 is an ALP (alkaline phosphatase) labeled antibody.

The immune complex 85 formed on the solid-state carrier 82 and the unreacted labeled substance 83 are separated from each other in a secondary B/F separation process. The B/F separator 180 executes each of steps of aspirating a liquid-phase substance and discharging a cleaning liquid under the magnetically attracting condition provided by the magnetic source 181 and performing stirring or shaking under the non-magnetically attracting condition once or multiple times. By the secondary B/F separation process, unnecessary components such as the unreacted labeled substance 83 are removed from inside the reaction container 93. At the end of the secondary B/F separation process, the immunoassay proceeds to the next step in a state where the liquid-phase substance in the reaction container 93 has been aspirated.

Then, the R4 reagent and the R5 reagent are dispensed into the reaction container 93 by the R4 reagent dispensing unit 163a and the R5 reagent dispensing unit 163b, respectively. The R4 reagent contains a buffer solution. The immune complex 85 bound to the solid-state carrier 82 is dispersed in the buffer solution. The R5 reagent contains a chemiluminescent substrate. The buffer solution contained in the R4 reagent has a composition that promotes a reaction between the label (enzyme) of the labeled substance 83 contained in the immune complex 85 and the substrate. After the dispensing of the R4 and R5 reagents, the specimen in the reaction container 93 is heated in the heater 150 to a predetermined temperature. Light is generated as the result of reacting the substrate with the label, and the intensity of the generated light is measured by the light detector 31 of the measurement unit 30. The content of the test substance 81 in the sample and the like are measured based on the detection signal of the measurement unit 30.

(Description of Operation for Measurement Process)

Figure 23:
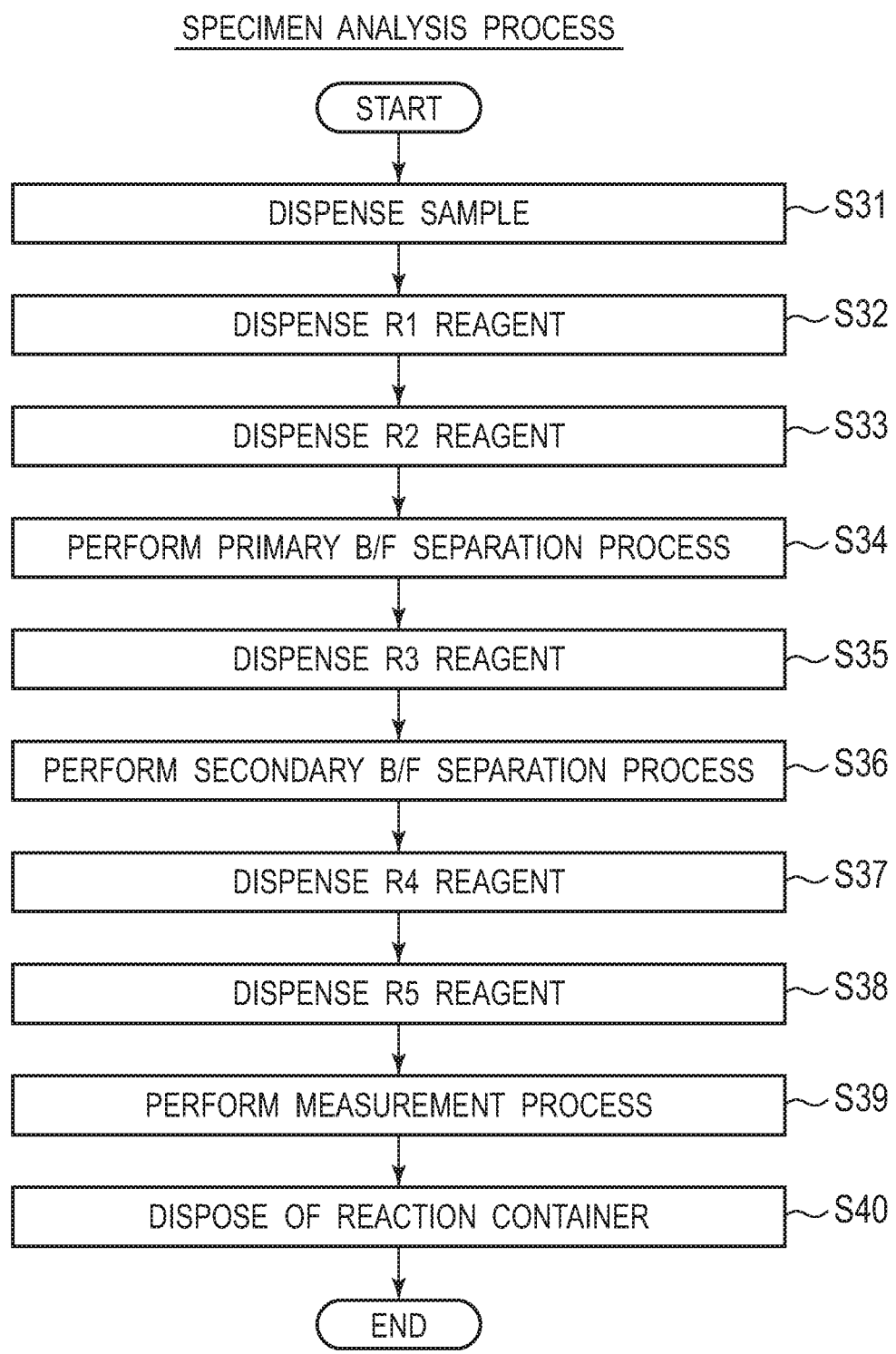
FIG. 23 is a flow diagram illustrating a measurement process, such as in FIG. 22.
Figure 24:
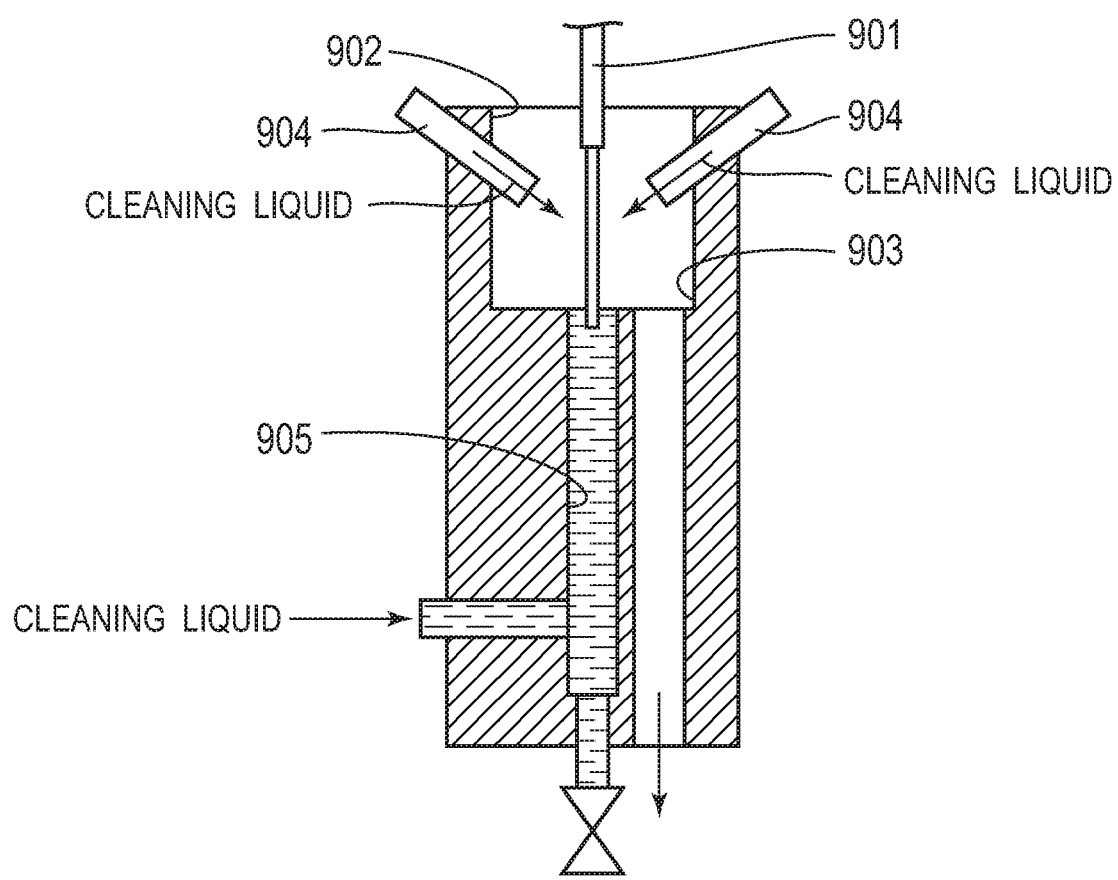
FIG. 24 is a diagram illustrating a conventional technique.

Next, the operation of the specimen measuring apparatus 100 for the measurement process illustrated in FIG. 22 is described using FIG. 23. Meanwhile, the process in each step illustrated in FIG. 23 is controlled by the controller 60 of the specimen measuring apparatus 100.

In step S31, a sample is dispensed into a reaction container 93. Specifically, a sample is aspirated by the aspiration tube 10a from a sample container 91 in the sample supply unit 126 of the sample transporter 120. The sample aspirated by the aspiration tube 10a is then dispensed into a reaction container 93. After the dispensing, the aspiration tube 10a is cleaned by the cleaning mechanism 50 by the above-described cleaning method with the cleaning liquid 70. The aspiration tube 10a is cleaned by the cleaning mechanism 50 each time it performs a dispensing operation.

In step S32, the R1 reagent is dispensed into the reaction container 93 by the aspiration tube 10b. After the dispensing, the aspiration tube 10b is cleaned by the cleaning mechanism 50 with the cleaning liquid. The aspiration tube 10b is cleaned by the cleaning mechanism 50 each time it performs a dispensing operation.

In step S33, the R2 reagent is dispensed into the reaction container 93 by the aspiration tube 10b. After the dispensing of the R2 reagent, the reaction container 93 is transferred to the heater 150 by the container transporter 140. The reaction container 93 is heated in the heater 150 for a predetermined time.

In step S34, the reaction container 93 is transferred to the B/F separator 180 by the container transporter 140. The B/F separator 180 performs the primary B/F separation process (see FIG. 22) on the specimen in the reaction container 93 to thereby remove its liquid component.

In step S35, the reaction container 93 is transferred to the R3 reagent dispensing position by the container transporter 140. Then, the R3 reagent is dispensed into the reaction container 93 by the aspiration tube 10b. After the dispensing of the R3 reagent, the reaction container 93 is transferred to the heater 150 by the container transporter 140. The reaction container 93 is heated in the heater 150 for a predetermined time.

In step S36, the reaction container 93 is transferred to the B/F separator 180 by the container transporter 140. The B/F separator 180 performs the secondary B/F separation process (see FIG. 22) on the specimen in the reaction container 93 to thereby remove its liquid component.

In step S37, the reaction container 93 is transferred to the R4 reagent dispensing position by the container transporter 140. The R4 reagent is dispensed into the reaction container 93 by the R4 reagent dispensing unit 163a.

In step S38, the reaction container 93 is transferred to the R5 reagent dispensing position by the container transporter 140. The R5 reagent is dispensed into the reaction container 93 by the R5 reagent dispensing unit 163b. After the dispensing of the R5 reagent, the reaction container 93 is transferred to the heater 150 by the container transporter 140. The reaction container 93 is heated in the heater 150 for a predetermined time.

In step S39, the reaction container 93 is transferred to the measurement unit 30 by the container transporter 140 and the transporter 125. The intensity of light generated by the reaction of the substrate with the label is measured by the measurement unit 30. The result of the detection by the measurement unit 30 is outputted to the analysis unit 300 via the controller 60.

In step S40 after the end of the detection, the transporter 125 takes out the reaction container 93 having finished the measurement process from the measurement unit 30 and disposes of it into a disposal port.

The operation of the specimen measuring apparatus 100 for the measurement process is performed in the above-described manner.

Note that the embodiments disclosed herein should be interpreted as exemplary in every aspect and not limiting. The scope of the present invention is indicated not by the description of the above embodiments but by the claims, and further encompasses all changes within meanings and scopes equivalent to the claims.

The invention claimed is:

1. A method of cleaning an aspiration tube in a specimen measuring apparatus, comprising:
    moving the aspiration tube from downward to upward while discharging a cleaning liquid onto an outer side surface of the aspiration tube, and stopping the upward movement of the aspiration tube in a state where a tip of the aspiration tube or a droplet attached to the tip contacts a surface of a flow of the cleaning liquid; and
    moving the stopped aspiration tube in a direction away from the surface of the flow of the cleaning liquid.

2. The method of cleaning an aspiration tube according to claim 1, wherein
    the discharging the cleaning liquid onto the outer side surface of the aspiration tube is performed inside a cleaning vessel, and
    the method further comprises moving the aspiration tube downward inside the cleaning vessel while continuously discharging the cleaning liquid onto the outer side surface of the aspiration tube and continuously draining the cleaning liquid from the cleaning vessel.

3. The method of cleaning an aspiration tube according to claim 2, wherein the moving the aspiration tube upward is performed after the moving the aspiration tube downward.

4. The method of cleaning an aspiration tube according to claim 1, further comprising moving the aspiration tube upward and downward while keeping the aspiration tube in contact with the flow of the cleaning liquid.

5. The method of cleaning an aspiration tube according to claim 2, wherein the moving the aspiration tube downward inside the cleaning vessel comprises discharging the cleaning liquid from the tip into the cleaning vessel by supplying the cleaning liquid into the aspiration tube.

6. The method of cleaning an aspiration tube according to claim 1, further comprising:
    obtaining position information on a position of the aspiration tube at which the tip of the aspiration tube or the droplet attached to the tip contacts the surface of the flow of the cleaning liquid, in a state where the cleaning liquid is not discharged onto the outer side surface of the aspiration tube, wherein
    the stopping the upward movement of the aspiration tube comprises stopping the upward movement of the aspiration tube based on the position information in the state where the tip of the aspiration tube or the droplet attached to the tip contacts the surface of the flow of the cleaning liquid.

7. The method of cleaning an aspiration tube according to claim 6, wherein the obtaining the position information comprises:
    detecting, by a liquid surface detector, contact of the tip of the aspiration tube or the droplet attached to the tip with the surface of the flow of the cleaning liquid; and
    obtaining the position information based on a result of the detecting by the liquid surface detector.

8. The method of cleaning an aspiration tube according to claim 6, wherein
    the obtaining the position information comprises moving the aspiration tube downward from above the flow of the discharged cleaning liquid so as to contact the tip or the droplet attached to the tip with the cleaning liquid, and
    the moving the aspiration tube while discharging the cleaning liquid comprises moving the aspiration tube upward, based on the position information, from a position at which the flow of the cleaning liquid contacts a portion of the aspiration tube above the tip of the aspiration tube to the position at which the tip or the droplet attached to the tip contacts the surface of the flow of the cleaning liquid.

9. The method of cleaning an aspiration tube according to claim 1, wherein the moving the aspiration tube while discharging the cleaning liquid comprises discharging the cleaning liquid obliquely downward so as to form a substantially straight columnar flow of the cleaning liquid.

10. The method of cleaning an aspiration tube according to claim 1, further comprising
    cleaning the aspiration tube with a second cleaning liquid higher in detergency than the cleaning liquid before the moving the aspiration tube while discharging the cleaning liquid.

* * * * *